United States Patent [19]
Steinhaus et al.

[11] Patent Number: 5,197,467

[45] Date of Patent: Mar. 30, 1993

[54] MULTIPLE PARAMETER RATE-RESPONSIVE CARDIAC STIMULATION APPARATUS

[75] Inventors: Bruce M. Steinhaus, Parker; Tibor A. Nappholz, Englewood; James A. Nolan, Conifer; Robert A. Morris, Palmer Lake; Ken Koestner, Englewood, all of Colo.

[73] Assignee: Telectronics Pacing Systems, Inc., Englewood, Colo.

[21] Appl. No.: 902,242

[22] Filed: Jun. 22, 1992

[51] Int. Cl.⁵ .................................. A61N 1/368
[52] U.S. Cl. .................. 128/419 PG; 128/734
[58] Field of Search ............ 128/419 PG, 419 P, 734, 128/671, 723

[56] References Cited

U.S. PATENT DOCUMENTS

| | | | |
|---|---|---|---|
| 4,140,132 | 2/1979 | Nappholz et al. | 128/419 PG |
| 4,428,378 | 1/1984 | Anderson et al. | 128/419 PG |
| 4,535,774 | 8/1985 | Olson | 128/419 PG |
| 4,567,892 | 2/1986 | Plicchi et al. | 128/419 PG |
| 4,692,719 | 9/1987 | Whigham | 332/11 D |
| 4,702,253 | 10/1987 | Nappholz et al. | 128/419 PG |
| 4,721,110 | 1/1988 | Lampadius | 128/419 PG |
| 4,860,751 | 8/1989 | Callaghan | 128/419 PG |
| 4,901,725 | 2/1990 | Nappholz et al. | 128/419 PG |
| 4,919,136 | 4/1990 | Alt | 128/734 |
| 4,926,863 | 5/1990 | Alt | 128/419 PG |
| 5,003,976 | 4/1991 | Alt | 128/419 PG |
| 5,063,937 | 11/1991 | Ezenwa et al. | 128/734 |

*Primary Examiner*—William E. Kamm
*Assistant Examiner*—George Manuel
*Attorney, Agent, or Firm*—Gottlieb, Rackman & Reisman

[57] ABSTRACT

A metabolic demand rate-responsive cardiac stimulation apparatus and method are disclosed which employ multiple physiological rate control parameters, such as respiratory minute volume, patient motion and cardiac stroke volume. The parameters are derived using a single standard pacing lead or transducer. The apparatus and method perform each physiological measurement by periodically applying a measuring current between two points within the apparatus. This measuring current has frequency components in a range of from approximately 10 kilohertz to 1000 megahertz. Application of this measuring current allows the apparatus to detect the voltage which arises from the applied current and, from the detected voltage, to measure the patient's spatial impedance. For a particular measurement, the apparatus controls which physiological parameter is sensed by regulating the frequency content of the measuring current. The apparatus analyzes the physiological parameters to determine the best pacing rate in terms of characteristics such as response time and stability.

44 Claims, 15 Drawing Sheets

MULTIPLE PARAMETER RATE-RESPONSIVE CARDIAC STIMULATION APPARATUS

TECHNICAL FIELD

The present invention relates to metabolic demand rate-responsive cardiac control devices, and more particularly to such devices having multiple metabolic demand sensors, the outputs of which are analyzed to derive a rate-control parameter.

BACKGROUND OF THE INVENTION

A general requirement for any rate-responsive pacemaker is a sensor for detecting a physiological parameter which varies with the body's metabolic demand for cardiac output of blood. Preferably, a rate-responsive pacemaker will monitor a physiological parameter which accurately responds to physical and emotional stimulation wherein changes in the parameter and in metabolic demand vary in a linear fashion. Various types of rate-responsive pacemakers have been developed which provide different approaches to metabolic-demand sensing. These pacemakers may measure different physiological parameters or measure a particular physiological parameter in a different manner to provide a basis for rate-adaptive pacing. Each of these different approaches to metabolic-demand sensing may be advantageous or disadvantageous for a particular patient or cardiac malfunction.

The present invention provides a rate-adaptive sensor within a pacemaker which allows the pacemaker to automatically match the pacing rate to the patient's metabolic demand and to respond quickly to changes in the metabolic demand. The operation of the sensor may be altered by means of programming of the pacemaker from an external communicating device. These alterations in sensor operation fulfill the needs of various patients who are afflicted with different cardiac and respiratory health problems. This sensor does not require special leads or special sensor transducers other than those common in standard cardiac pacemakers.

One common metabolic-demand sensor measures physical activity to provide a suitable parameter for rate adaptation. A physical activity sensor is not generally regarded as a truly physiologic sensor because it does not measure true metabolic demand and, therefore, is not affected by emotional stimuli or pyrexia. In U.S. Pat. No. 4,140,132, entitled "Variable Rate Timer for a Cardiac Pacemaker", issued to J. D. Dahl on Feb. 20, 1979, a pacemaker employs an accelerometer, an implanted weighted cantilever arm piezoelectric crystal, to monitor the physical activity of a patient and set the pacemaker's escape interval. Similarly, in U.S. Pat. No. 4,428,378, entitled "Rate Adaptive Pacer", issued on Jan. 31, 1984, K. M. Anderson et al. describe a sensor which generates a signal reflecting the activity of a patient. The pacemaker bandpass filters this signal, detects its amplitude and derives a pacing rate from the processed signal. The high frequency content of this signal increases with patient movement, therefore the pacemaker modulates the pacing rate, between preset rate maxima and minima, in proportion to the intensity of the processed signal.

The most important advantage of a physical-activity sensor is its very rapid response time to the onset of exercise. A physical-activity sensor responds favorably to patient activities which create vibration, such as jogging, walking and stair climbing. Unfortunately, activities such as bicycling do not promote rate adaptation because little vibration occurs.

Further advantages of a physical-activity sensor lie in its simplicity. No special pacing lead is required since an activity-based pacemaker may employ standard leads with either unipolar or bipolar electrodes. Furthermore, no special implanting procedure is required for an activity-based pacemaker.

Although the lack of a truly physiological response is generally considered a disadvantage of an activity sensor, the fact that this sensor acts independently from physiologic variables may provide a better response under conditions in which patient systems or tissues are diseased. For example, an activity sensor may supply a better signal for responding to exercise than a respiration sensor will under conditions of lung disease, such as emphysema.

The primary disadvantage of a rate-responsive pacemaker employing a physical-activity sensor is the difficulty of attaining a scaled response to gradations of metabolic demand. Activity sensors generally act in an on/off fashion, in which a sensor is unable to detect changes in patient workload. Therefore, the response of activity-based, rate-responsive pacemakers does not normally depend on the amount of exercise the patient is performing, but instead the rate change remains identical so long as the measured activity is above a preprogrammed level. Because it is difficult or impossible to relate the amount of vibration of the sensor to the cardiac output needs of a patient performing activity of various types, the sensor cannot be programmed to adapt the pacing rate in a physiological manner. In particular, it is difficult to program the pacemaker to correctly respond to the onset or cessation of exercise.

Furthermore, a physical-activity sensor generates an undesirable response to noise disturbances arising external to the body (e.g., machinery) or from within the body (e.g., coughing, sneezing and laughing). Also, noise signals tend to swamp activity-induced signals which occur at some frequencies.

A second type of metabolic-demand sensor measures and analyzes impedance signals which relate to cardiac mechanical performance to adapt the pacing rate to the metabolic demands of the patient. Pacemakers analyze and process cardiac mechanical data to derive physiological parameters such as stroke volume or cardiac output. For example, a pacemaker may utilize an intravascular-impedance sensor to measure right ventricular stroke volume and adjust pacing rate to keep this parameter at predetermined physiologic values. In U.S. Pat. No. 4,535,774, entitled "Stroke Volume Controlled Pacer", issued on Aug. 20, 1985, W. H. Olson describes an impedance plethysmography sensor, comprising a number of electrodes and analysis circuitry, which is employed to detect variations in stroke volume over time. The pacemaker sets the pacing rate according to these changes in stroke volume.

The primary advantage of using stroke volume as a parameter for adjusting rate in a rate-responsive pacemaker is the capability of rapidly adjusting the rate to changes in metabolic demand in a physiologic manner.

The main disadvantage of the stroke-volume, rate-responsive pacemaker is its requirement for a nonstandard pacing lead having multiple electrodes. Sensing of impedance using standard bipolar leads has not provided the accuracy in the stroke volume measurement which is necessary for rate-adaptive control. Preferable tripolar or quadripolar leads have not been durable enough for chronically implanted usage. Furthermore, an appropriate algorithm for driving a closed loop adaptive pacing rate has not been discovered. Rate-response algorithms using stroke volume as a control parameter have been most ineffective for sick patients. A disadvantage of stroke-volume controlled rate adaptation, in comparison to rate control based on physical activity, is its requirement for complex sensors and circuits and an inability to use standard pacing leads.

Another type of metabolic-demand sensor measures and analyzes impedance signals which relate to a patient's respiratory function to adjust pacing according to the metabolic demands of the patient.

In U.S. Pat. No. 4,567,892, entitled "Implantable Cardiac Pacemaker", issued to G. Plicchi and G. Canducci on Feb. 4, 1986, a pacemaker is disclosed which monitors respiratory rate by measuring impedance variations throughout a distance within the thoracic region of a patient's body, between the pacemaker can and a separate auxiliary or passive lead implanted subcutaneously in the chest wall using a special tunneler. A programmed algorithm within the pacemaker analyzes the respiratory rate to determine a pacing rate. It has been shown that heart rate, respiratory rate and oxygen uptake all correlate well irrespective of the presence of lung disease. All parameters increase at the onset of exercise and decrease when exercise stops. The rate-responsive pacemaker which is driven by the respiration rate measurement is simple and reliable, as well as sound in its physiologic basis.

A fundamental disadvantage of driving the pacing rate on the basis of respiratory-rate variations is that it takes into account only part of the body's ventilation adaptation in response to exercise. Ventilation increases due to an increase in the depth of respiration as well as the respiration rate. Although respiratory rate relates somewhat closely to heart rate, heart rate correlates much more strongly with the total amount of inspired air. That the Plicchi and Canducci pacemaker requires a special surgical procedure, tunneling of a lead in the patient's thoracic region, and a special sensor, are practical disadvantages of the device.

M. S. Lampadius, in U.S. Pat. No. 4,721,110, entitled "Respiration-controlled Cardiac Pacemaker", issued on Jan. 26, 1988, improves on the respiration-rate-driven pacemaker by disclosing a pacemaker driven either by respiration depth or respiration rate. This pacemaker employs a rheography pulse generator, which generates constant amplitude pulses during the refractory period of a patient's heart, and a respiration detector which, as a function of the impedance data measured in response to the rheography pulses, generates a respiration signal representing the respiratory rate, the depth of respiration or a combination of the rate and depth of respiration. The pacemaker then uses this respiration signal to determine an appropriate pacing stimulation rate.

The respiratory parameter which correlates most closely to heart rate is minute ventilation, a highly physiologic variable which reflects closely the metabolic demands of exercise. The body's increase in minute ventilation during exercise parallels its oxygen uptake but also reflects changes in cardiac output and heart rate. Minute ventilation not only correlates well with exercise, but also varies in response to stress and pyrexia. U.S. Pat. No. 4,702,253 (hereinafter called the "'253 patent"), entitled "Metabolic-Demand Pacemaker and Method of Using the Same to Determine Minute Volume", issued to T. A. Nappholz et al. on Oct. 27, 1987, discloses a rate-responsive pacemaker which senses impedance in the pleural Cavity of a patient and derives respiratory minute volume from impedance. The pacemaker then employs the respiratory minute volume, a measure of the amount of air inspired by a person as a function of time, as a rate-control parameter. The greater the amount of air inspired, the greater the need for a higher pacing rate. The device described in this patent requires a nonstandard pacing lead in order to perform the minute volume measurement.

U.S. Pat. No. 4,901,725 (hereinafter called the "'725 patent"), entitled "Minute Volume Rate-Responsive Pacemaker", issued to T. A. Nappholz et al. on Feb. 20, 1990, discloses a pacemaker which performs a rate-responsive function in the manner of the '253 patent with various improvements, and, in addition, only requires standard pacing leads. To measure the intravascular impedance, the minute-volume sensor generates a low energy current pulse at 50 ms intervals between a ring electrode of the lead and the pulse generator case, then measures the voltage between the tip electrode of the lead and the pulse generator case arising from the applied current. An intravascular impedance value is determined from the measured voltage and the applied current using Ohm's law. Transthoracic impedance increases with inspiration, decreases with expiration and its amplitude varies with the tidal volume. The impedance signal thus comprises two components, representing tidal volume and respiratory rate. Pulse generator circuitry identifies the two signals and processes them to yield minute ventilation. The minute-volume-controlled rate-responsive pacemaker employs a highly physiologic sensor. Its ability to assess the metabolic demands of the body are superior to that of a pacemaker driven by respiratory rate alone, since depth of ventilation is an important response to exercise or stress. The apparatus described in the '725 patent requires no more than standard pacing leads, although the leads cannot be unipolar leads, and programming of minute ventilation rate adaptation necessitates only a single exercise test.

Pacemakers which use any of the discussed respiratory parameters as a basis for rate adaptation are considered to respond more slowly to the onset of exercise than a physical activity controlled pacemaker. A faster response is more desirable.

An advantage of the activity-sensing pacemakers is its fast response to the onset of exercise, but a major disadvantage of a pacemaker which determines pacing rate based on an activity signal alone is its substantial inability to react to the instantaneous metabolic level of exercise or stress. A pacemaker which uses a more physiologic parameter may respond less quickly to the onset of exercise, but is highly specific with respect to the metabolic level of exercise. Thus, a pacemaker may employ two parameters in combination in a rate adaptive cardiac pacing system, wherein each parameter complements the other by mutually supplying what the other lacks.

U.S. Pat. No. 4,926,863, entitled "Rate-responsive Cardiac Pacemaker", issued to E. Alt on May 22, 1990, discloses a rate-responsive cardiac pacemaker which employs an activity sensor, in the form of an accelerometer, as a first sensor of metabolic demand and a second sensor which is adapted to detect a parameter which is complementary to activity. The measurement of the second sensor is used to supply a "complementary parameter" for confirming the presence of a particular metabolic state and selectively contributing to the determination of a stimulation rate. The complementary parameter of the second sensor is defined as any physiological or other detected parameter, within or outside the body, having characteristics of sensitivity and specificity to physical exercise which contrast and enhance the corresponding characteristics of the activity sensor, specifically, a fast response time to the onset of exercise but nonspecificity with respect to the instantaneous metabolic level of exercise. The Alt patent mentions the parameter of central venous blood temperature as a possible complementary parameter.

U.S. Pat. No. 4,860,751, entitled "Activity Sensor for Pacemaker Control", issued to F. J. Callaghan on Aug. 29, 1989, also discloses a rate-responsive cardiac pacemaker which includes an activity sensor in combination with a second sensor for monitoring a physiological parameter such as partial pressure of oxygen ($pO_2$), blood pressure, core temperature, $CO_2$ and $pCO_2$, $O_2$ and $pO_2$, pH, respiration rate, respiration depth and ventricular volume. In this patent, the activity sensor provides for generally constant monitoring of patient motion. When patient motion causes the activity sensor to generate a signal exceeding a preset threshold level, the physiological sensor is activated. The parameter generated by the physiological sensor is used to set pacing rate. The advantage of using an activity sensor as a trigger to initiate sensing by a physiological sensor is that the activity sensor requires very little energy expenditure to operate. In contrast, a physiological parameter sensor normally consumes a great deal of energy.

SUMMARY OF THE INVENTION

In accordance with one aspect of the present invention, there is provided a metabolic-demand, rate-responsive cardiac stimulation apparatus which paces a patient's heart at a controlled rate. The apparatus analyzes a signal from an impedance-measuring sensor within the patient's body to determine this controlled rate. This sensor applies multiple fixed frequencies of current between two points within the apparatus and measures voltages in response to the application of the measuring currents. The measuring current is in the form of a measuring signal having frequency components within a range from approximately 10 kilohertz to approximately 1000 megahertz. The apparatus includes a means for controlling the impedance sensor, which limits the frequency components of the applied time-varying current to lie within at least one predetermined subrange of frequencies. For each subrange of measuring frequencies, the measured voltage arising in response to the applied current corresponds to a measurement of a particular metabolic-demand parameter. The apparatus further includes a means to derive at least one metabolic-demand parameter from the measured voltage corresponding to each predetermined subrange of frequencies. A means for determining the controlled pacing rate sets the rate in terms of a predefined relationship or rate to the values of at least one of the derived metabolic-demand parameters.

The means for pacing a patient's heart at a controlled rate within the apparatus of the present invention includes at least one pacing lead. In some embodiments of the present invention, the impedance-measuring sensor applies a measuring current and measures the voltage resulting from the applied measuring current by means of at least one electrical coupling to a pacing lead. The other electrical coupling of the impedance-measuring sensor may either connect with a point within the apparatus, such as its case, or may connect with another lead, if one is included within the apparatus.

The apparatus may also include a transmission coil, for example, a coil that is commonly used to perform telemetric communication. In embodiments of the invention which are an alternative to embodiments in which the impedance-measuring sensor couples to at least one lead, this sensor may couple to the coil to generate measuring current and measure the resulting voltage. An implementation of the apparatus which employs a coil to sense impedance provides a different signal for analysis than an implementation employing a pacing lead. The coil can measure mechanical movement of the heart alone, whereas the lead measures mechanical movement in combination with blood flow. (Note that a lead which is insulated at its tip also senses mechanical movement of the heart without a signal component relating to blood flow.) A coil which is affixed within the pacemaker case can still sense impedance.

A coil may be affixed to the end of a pacemaker lead to sense impedance in its vicinity. The signal produced by sensing impedance from a coil at the end of a lead differs from the signal produced by sensing impedance from the lead itself, since the lead will sense impedance along its entire length while the coil will sense only locally, at the tip of the lead.

The impedance-measuring sensor generates measuring current in the form of either short-duration, square-wave-like current pulses, sinusoidal-like oscillating current or short-duration pulses of sinusoidal-like oscillating current. Current pulses range in duration from 5 ns to 20 $\mu$s. Oscillating current ranges in frequency from 10 kHz to 1000 MHz, and may be generated continuously or in pulses as short as 5 ns.

If the impedance-measuring sensor generates measuring current on a pacing lead in the form of short-duration, square-wave-like current pulses or short-duration pulses of sinusoidal-like oscillating current, the sensor control means sets the value of the duration for the purpose of measuring a particular metabolic-demand parameter. One possible metabolic-demand parameter is based on patient motion. Its associated subrange of durations includes pulse durations shorter than approximately 125 nanoseconds. A second possible metabolic-demand parameter is based on respiration and its associated subrange of durations includes pulse durations from approximately 50 nanoseconds to approximately 400 nanoseconds. A third possible metabolic-demand parameter is based on cardiac hemodynamic signals. Its associated subrange of durations includes pulse durations longer than approximately 300 nanoseconds.

If the impedance measuring sensor generates measuring current on a pacing lead in the form of sinusoidal-like oscillating current, the sensor control means sets the value of the sinusoidal-like oscillating frequency for the purpose of measuring a particular metabolic-demand parameter. One possible metabolic-demand parameter is based on patient motion. Its associated subrange of frequencies includes those higher than approximately 8 megahertz. A second possible metabolic-demand parameter is based on respiration and its associated subrange of frequencies ranges from approximately 1 megahertz to approximately 11 megahertz. A third possible metabolic-demand parameter is based on cardiac hemodynamic signals. Its associated subrange of frequencies is the range less than about 4 megahertz.

In some embodiments of the invention, if the impedance measuring sensor generates measuring current in the form of pulses, the sensor control means sets the value of the duration for the purpose of measuring a particular metabolic-demand parameter. The sensor control means may consistently set the duration to a single value to measure only one metabolic parameter. Alternatively, the sensor control means may set a number of duration values and interleave (in time) current pulses with different durations to measure multiple metabolic parameters. The sensor control means may time the different duration pulses to take place in any sequence so that different sampling rates may apply to the pulse of varying duration.

In embodiments of the invention which are alternative to embodiments in which the sensor control means varies the measuring-pulse duration, the sensor control means generates short-duration, square-wave-like current pulses or short-duration pulses of sinusoidal-like oscillating current to a particular predefined duration and sets the timing of each voltage measurement for the purpose of measuring a particular metabolic-demand parameter. For each current pulse, the impedance-measuring sensor may sample the voltage at one or more times. These sampling times are set by the sensor control means. Each of these voltage sampling times defines a sampling duration which begins at the onset of the current pulse. The sensor control means may set multiple sampling durations to allow the impedance-measuring sensor to measure multiple metabolic parameters. The sampling durations in these alternative embodiments of the invention produce signals which are equivalent to the same measuring-current-pulse durations in embodiments of the invention in which the impedance-measuring sensor generates measuring-current pulses of different durations.

The present invention incorporates two or more rate-adaptive sensors in a single rate-responsive pacing apparatus. These multiple sensors reside in a single circuit which requires only standard bipolar and unipolar pacing leads, rather than special, nonstandard pacing leads. The multiple sensors do not need special sensor transducers other than the sensing circuits which are common in the field of cardiac pacemakers. Appropriate selection of these sensors provides for automatic matching of the pacing rate to the patient's metabolic demand and to respond quickly to changes in the metabolic demand. The selection and control of these sensors may be altered by means of programming of the pacemaker from an external communicating device. Thus, a physician may activate one or more sensors to provide a rate-adaptive parameter which is best suited to a patient, thereby fulfilling the needs of various patients who are afflicted with different cardiac and respiratory health problems.

The present invention provides a single pacing apparatus in which a single impedance-measuring sensor may measure completely separate metabolic-demand parameters employing independent analysis procedures. A physician may select the metabolic parameter and analysis method most suitable for a patient. Alternatively, the physician may enable a more complex analysis system in which the sensed metabolic-demand parameters are combined via a control logic such that deficiencies in the response to one sensed parameter can be overcome by another. For example, rapid response of activity may be combined with stable response of minute ventilation.

BRIEF DESCRIPTION OF THE DRAWINGS

Further objects, features and advantages of the invention will become apparent upon consideration of the following detailed description in conjunction with the accompanying drawings, in which.

DETAILED DESCRIPTION

Figure 1:
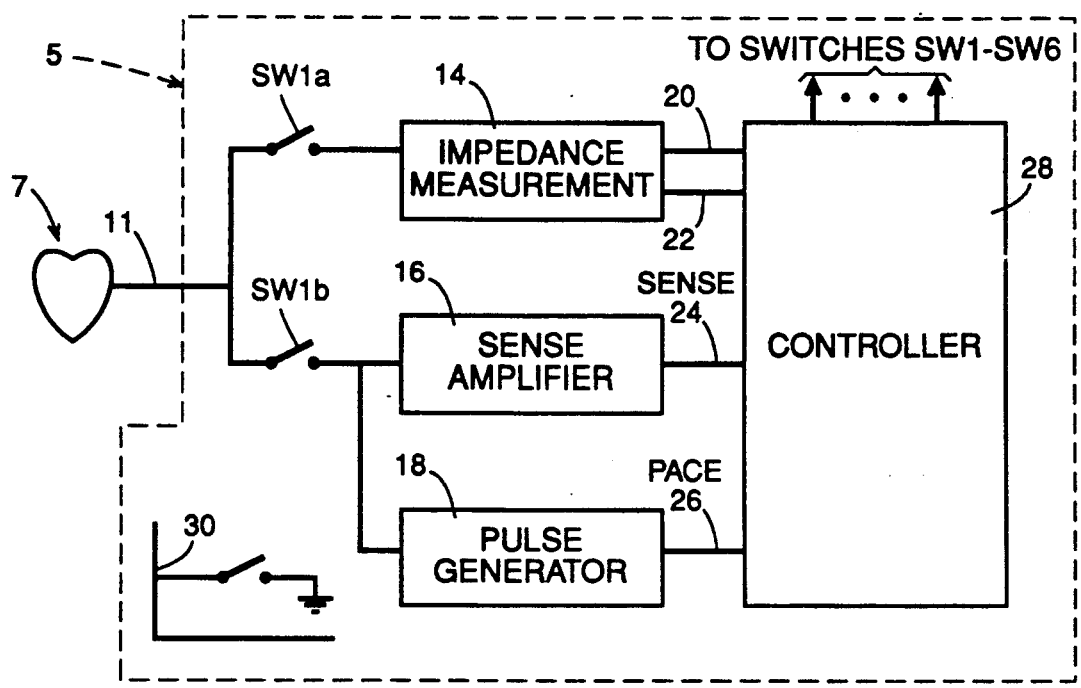
FIG. 1 is a block diagram of an illustrative embodiment of the invention.
Figure 14:
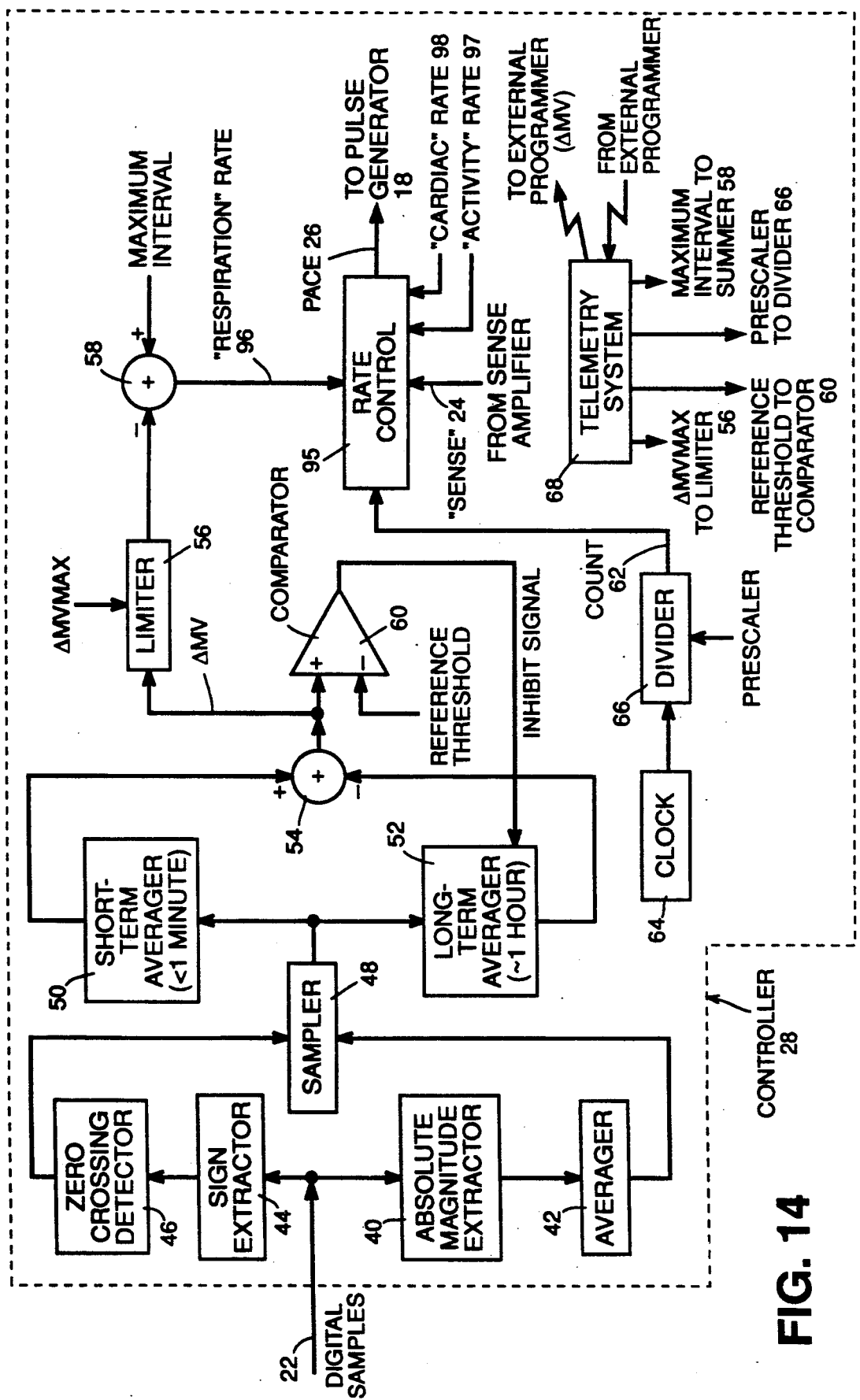
FIG. 14 depicts circuit blocks, contained in a controller shown in block form in FIG. 1, which operate on digital samples of the impedance measurement to derive "respiration" rate commands that are sent to a rate controller.

The drawing of FIG. 1 is a high-level block schematic of the apparatus of the invention in the form of a pacemaker, shown generally at 5. All pacemaker logic is under the control of a controller 28 (which may include a microprocessor, although discrete blocks are shown in FIG. 14). The controller operates various switches in the pacemaker, of which only one pair SW1a, SW1b is shown. Switch SW1b is closed whenever the pacemaker is to pace or sense.

Figure 2:
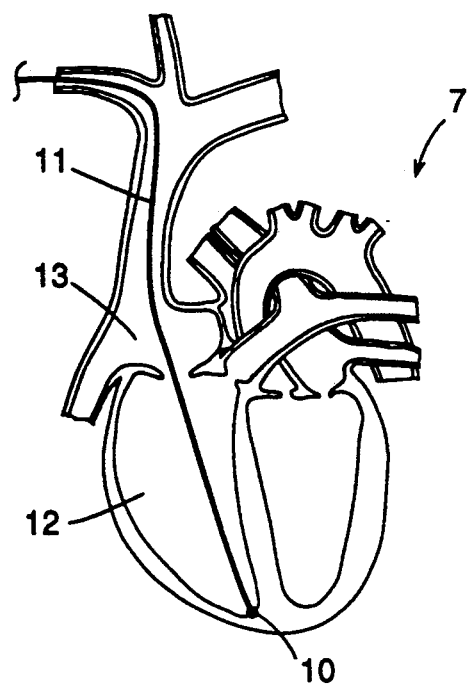
FIG. 2 depicts placement in a patient's right ventricle of a conventional unipolar lead which may be used to effect minute-volume measurements, along with pacing and sensing.

Referring to FIGS. 1 and 2, together, in order to pace, the controller 28 sends a command to a pulse generator 18 by means of a signal on a PACE conductor 26. The pulse generator 18 responds to this command by applying a current pulse through the switch SW1b and a conventional unipolar pacing lead 11 to the latter's tip electrode 10, which is shown positioned in the right ventricle 12 of a patient's heart 7 in FIG. 2. A sense amplifier 16 senses a cardiac signal on the electrode. (Various functions well known in the art, such as blanking of the sense amplifier during pacing, are not shown inasmuch as they have no bearing on the subject invention.) The sensing of a heartbeat, spontaneous or evoked, results in a pulse appearing on a SENSE conductor 24 for communication to controller 28. The "SENSE" function activates the loading of an initial "count" value 62 (FIG. 18), as will be described hereinafter.

The pacemaker 5 makes an impedance measurement when the controller 28 pulses the conductor 20 to activate impedance measurement circuit block 14. Upon this event, switch SW1a closes, switch SW1b opens and impedance measurement circuit block 14 applies a current to the lead 11, causing current to flow through the lead toward the tip electrode 10. The measuring current which is applied to the electrode has frequency characteristics in the range from about 10 kHz to about 1000 MHz. At these measuring current frequencies, the lead acts as an antenna which creates a displacement current in the body. This displacement current is fundamentally different from the conduction current which is generated by prior art impedance-measuring pacemakers such as those shown in the aforementioned '253 and '725 patents. The impedance measurement circuit block 14 may generate this measuring current in the form of sinusoidal-like oscillating current, short-duration pulses of square-wave-like current, or timed pulses of sinusoidal-like oscillating current. The impedance measurement circuit block 14 measures spatial impedance by determining the potential between the pacemaker case 30 and the pacemaker's input connection to the conductor (not shown) within lead 11. This conductor extends to the tip electrode 10. In this configuration, the pacemaker case 30 serves as a reference potential for the pacemaker circuitry. In the preferred embodiment of the pacemaker, the impedance measurement circuit block 14 derives samples at a rate of about 20 per second and communicates these samples to controller 28 over conductor 22. The impedance measurement can be executed as described in the aforementioned '253 patent.

Placement of the unipolar lead 11 is shown in FIG. 2. The tip electrode 10 makes contact with the wall of the right ventricle 12 or the right atrium 13 of the patient's heart 7. When the impedance measurement circuit block 14 generates measuring currents at appropriate frequencies, as will be described hereinafter, the impedance measurement reflects minute volume to a much greater extent than stroke volume or motion artifacts. In addition, the impedance measurement reflects minute volume more than signals originating from other physiological and non-physiological sources because of the characteristics of a filter 23 (FIG. 3) which is part of the impedance measurement circuit (see, also, FIG. 1 of the '253 patent). In an embodiment of the invention which filters the impedance signal to favor sensing of a respiration signal component over other components, the impedance signal is filtered by a two-pole filter with a center frequency of 0.2 Hz. The gain is reduced by a factor of two (6 dB) at frequencies of 0.05 Hz and 0.8 Hz. Alternatively, the capacitors and resistors of the circuit of filter 23 may be chosen to preferentially elicit other physiological signal components. For example, the cutoff frequencies for a bandpass filter which favors cardiac hemodynamic signals may range from 0.2 to 10 Hz. Furthermore, the cutoff frequencies for a bandpass filter which best supports patient motion signals may range from 5 to 10 Hz.

Figure 3:
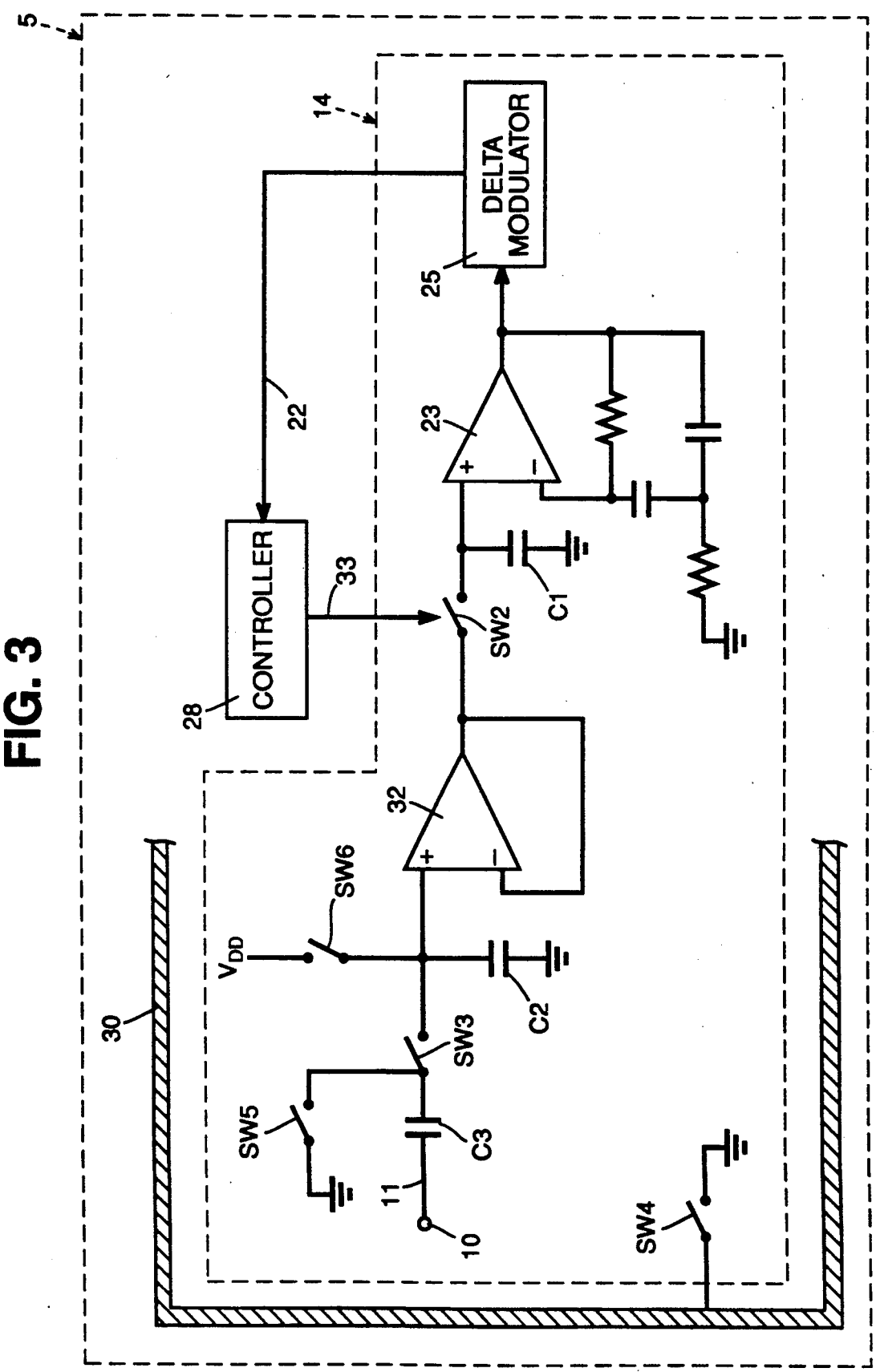
FIG. 3 depicts one embodiment of an impedance measurement circuit, shown in block form in FIG. 1, which operates in a pulsed mode, rather than a sinusoidal-like oscillating mode.

Referring to FIG. 3, an embodiment of the impedance measurement circuit 14 which operates in a pulsed mode is shown. The impedance measurement circuit 14 includes a connection through a switch SW4 with the pacemaker case 30, and a connection through a switch SW3 with the tip electrode 10 (via the pacing lead 11). The tip electrode 10 is a conventional pacing/sensing electrode. The indifferent electrode is the case 30. The impedance measurement circuit 14 employs the tip electrode 10 and lead 11 both for applying a source measuring current to the patient's body, and for measuring the impedance between the tip electrode 10, lead 11 and the case 30. A buffer 32 (which is discussed hereinafter) and the filter 23 are also employed in circuit 14.

All switches in FIG. 3 are directly or indirectly under the control of controller 28. One output 33 of the controller is shown extended to switch SW2, but it is to be understood that the switches SW3, SW4, SW5, SW6, SW1a and SW1b are similarly controlled. The controller closes switch SW6 to charge a measuring capacitor C2 to a regulated voltage source VDD. Subsequently, the controller opens switch SW6 and closes switches SW3 and SW4, while holding switch SW5 open, for a predetermined measuring interval ΔT, thereby connecting capacitor C2 to lead 11 through a coupling capacitor C3. While the switches SW3 and SW4 are closed, measuring capacitor C2 discharges through capacitor C3 into the lead 11, thereby decreasing the voltage across measuring capacitor C2. The amount by which the voltage across the measuring capacitor C2 diminishes depends on the impedance of the lead-tip combination and the impedance of the surrounding tissue. The impedance of the lead-tip combination is known and the impedance of the surrounding tissue is the object of the measurement.

Measuring capacitor C2 stores the diminished voltage and buffer 32 later transfers this to the measuring circuit in the following manner. After the predetermined measuring time interval $\Delta T$, the controller 28 opens switches SW3 and SW4, allowing the buffer 32 to access the voltage held on the measuring capacitor C2. This voltage is advanced through the buffer amplifier 32 and switch SW2 (which the controller 28 closes at the time it opens switches SW3 and SW4), and is sampled on capacitor C1 at the input of the filter 23. The controller 28 holds switch SW2 closed for a time duration which is sufficient for a delta modulator 25 to convert the signal into a digital form. For example, a delta modulator which is capable of low current operation in an implantable device may commonly convert a signal to digital form in about 1 millisecond.

Switch SW1a is closed during the previously described impedance measurements. However, the controller 28 may occasionally command the performance of a noise measurement by opening switches SW1b, SW5, SW6 and while closing switches SW1a, SW4, and SW2. The controller 28 may thus acquire a noise measurement and compare the noise signal with an impedance measurement signal to evaluate errors resulting from noise.

Resuming consideration of the impedance measurements, after converting the sample to digital form, the controller 28 opens switch SW2 and closes switch SW6 to charge measuring capacitor C2 for the next measurement cycle. In the preferred embodiment of the invention, the controller 28 measures impedance twenty times per second. For each measurement, the controller closes the switches SW3 and SW4 for a pulse duration of 250 ns, during which the voltage across the measuring capacitor C2 is placed on the lead 11. The resistors and capacitors associated with filter 23 pass frequencies between about 0.05 Hz and 0.8 Hz, the standard range for respiratory measurements.

The value of the measuring capacitor C2 is selected to store the range of voltages which result from various body impedances. In one embodiment of the invention, C2 has a capacitance of 4.7 nF.

The coupling capacitor C3 provides DC isolation for the input to the measuring circuit. In one embodiment of the invention, a coupling capacitor C3 has a value of about 7.5 $\mu$F, which effectively eliminates the influence of the DC voltage on measurement results.

As indicated earlier, the analog signal output of filter 23 passes to delta modulator 25 which provides a digital signal output on conductor 22. The digital signal output on conductor 22 is input to controller 28 for processing, as is hereinafter described in connection with a discussion of FIG. 14. Converting an analog signal to a digital representation by delta modulation is a standard technique. One example of such an operation is illustrated in U.S. Pat. No. 4,692,719 to Robert H. Whigham, entitled "Combined Pacemaker Delta Modulator and Bandpass Filter", which issued on Sep. 8, 1987. The output of delta modulator 25 is a summation of a series of 0's and 1's which reflect whether the analog signal is decreasing or increasing.

During a measurement interval, controller 28 opens switch SW1b (shown in FIG. 1) to briefly disable pace and sense functions. Although sensing is disabled while the impedance measurement is in operation, the duration of the measurement is on the order of fractions of microseconds, a time so short relative to that of heart signals that disabling sensing during this time is of no importance.

Figure 4:
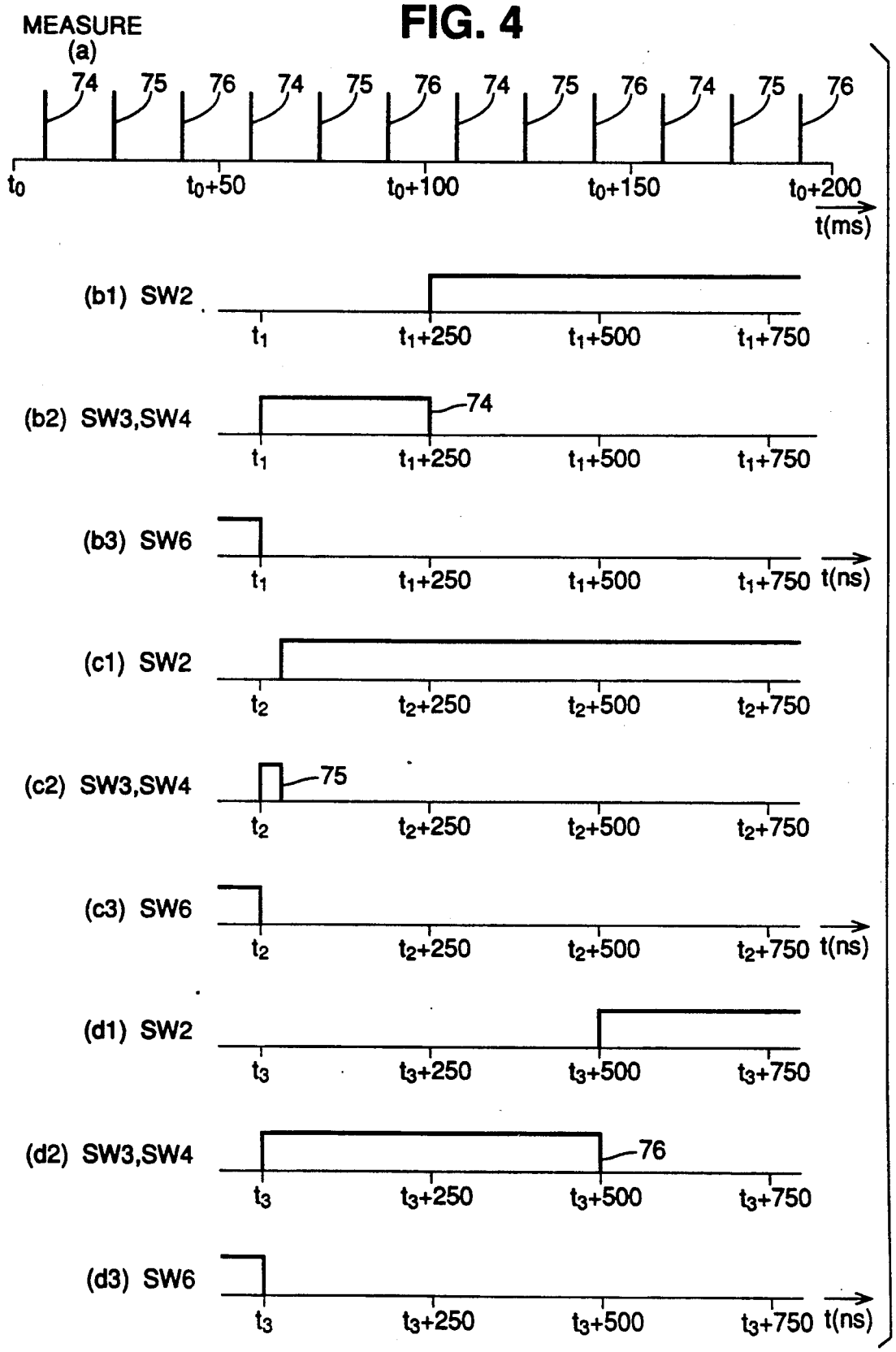
FIG. 4 shows waveform timing diagrams which are useful in understanding the operation of one implementation of the impedance measurement circuit, shown in FIG. 3.

Referring now to FIG. 4 waveform timing diagrams are shown which indicate one method by which the controller 28 may regulate switches SW2-SW4 and SW6 within the impedance measurement circuit 14 to measure three different physiological parameters—patient motion (also called activity), respiration and cardiac signals indicative of stroke volume. Referring to line (a) of FIG. 4, controller 28 samples respiration, patient motion and stroke volume by means of sampling pulses 74, 75 and 76, respectively. The controller regulates continuous, interleaved, sampling of each of the three physiological parameters, sequentially, at 50 millisecond intervals for each type, and with 16.67 milliseconds separating the beginning of each sample from adjacent dissimilar samples. The selection of a 50 millisecond sampling interval is made to illustrate the operation of the switches of FIG. 3 and the method of sampling. It is to be understood that other sampling intervals are intended to be included within the scope of the invention. For example, the various physiological signal components are likely to be sampled at different intervals. Cardiac hemodynamic signals may be sampled at a higher rate (e.g. 10 millisecond intervals) but only during the time blood is ejected from the heart following depolarization of the heart (e.g., from 80 milliseconds to 280 milliseconds after an R-wave).

Controller 28 has complete control of the sampling procedure. For example, the controller may enable or disable the sampling for any of the parameters, may individually change the intervals between samples relating to a particular parameter or may change the ratio of sampling for one parameter in relation to another.

Lines (b1)–(b3) of FIG. 4 illustrate one example of a procedure by which controller 28 may regulate the sampling of the respiration parameter. The controller starts the sampling procedure at $t_1$ by opening switch SW6 ((line (b3) goes low)) and closing switches SW3 and SW4 ((line (b2) goes high)) for 250 nanoseconds. Next, at $t_1+250$, the controller 28 opens switches SW3 and SW4 ((line (b2) goes low)) and closes switch SW2 ((line (b1) goes high)) to allow delta modulator 25 (of FIG. 3) to convert the signal to a digital number. Switch SW2 is held closed for the time duration required to digitize the sample (for example, 1 millisecond). The controller then opens switch SW2 and closes switch SW6 (action not shown) to finish the sampling procedure and charge the capacitor C2 (of FIG. 3).

In the same manner, lines (c1)–(c3) of FIG. 4 depict an example of the procedure by which controller 28 regulates the sampling of the patient motion parameter. The controller starts the sampling procedure at $t_2$ by opening switch SW6 ((line (c3) goes low)) and closing switches SW3 and SW4 ((line (c2) goes high)) for 25 nanoseconds. At the end of the 25 nanoseconds, switches SW3 and SW4 open ((line (c2) goes low)) and switch SW2 closes ((line (c1) goes high)).

In the same manner, lines (d1)–(d3) of FIG. 4 depict an example of the method by which the controller 28 regulates the sampling of the stroke volume parameter. The controller 28 starts the sampling procedure at $t_3$ by opening switch SW6 ((line (d3) goes low)) and closing switches SW3 and SW4 ((line (d2) goes high)) for 500 nanoseconds. At the end of the 500 nanoseconds, switches SW3 and SW4 open ((line (d2) goes low)) and switch SW2 closes ((line (d1) goes high)).

Figure 5:
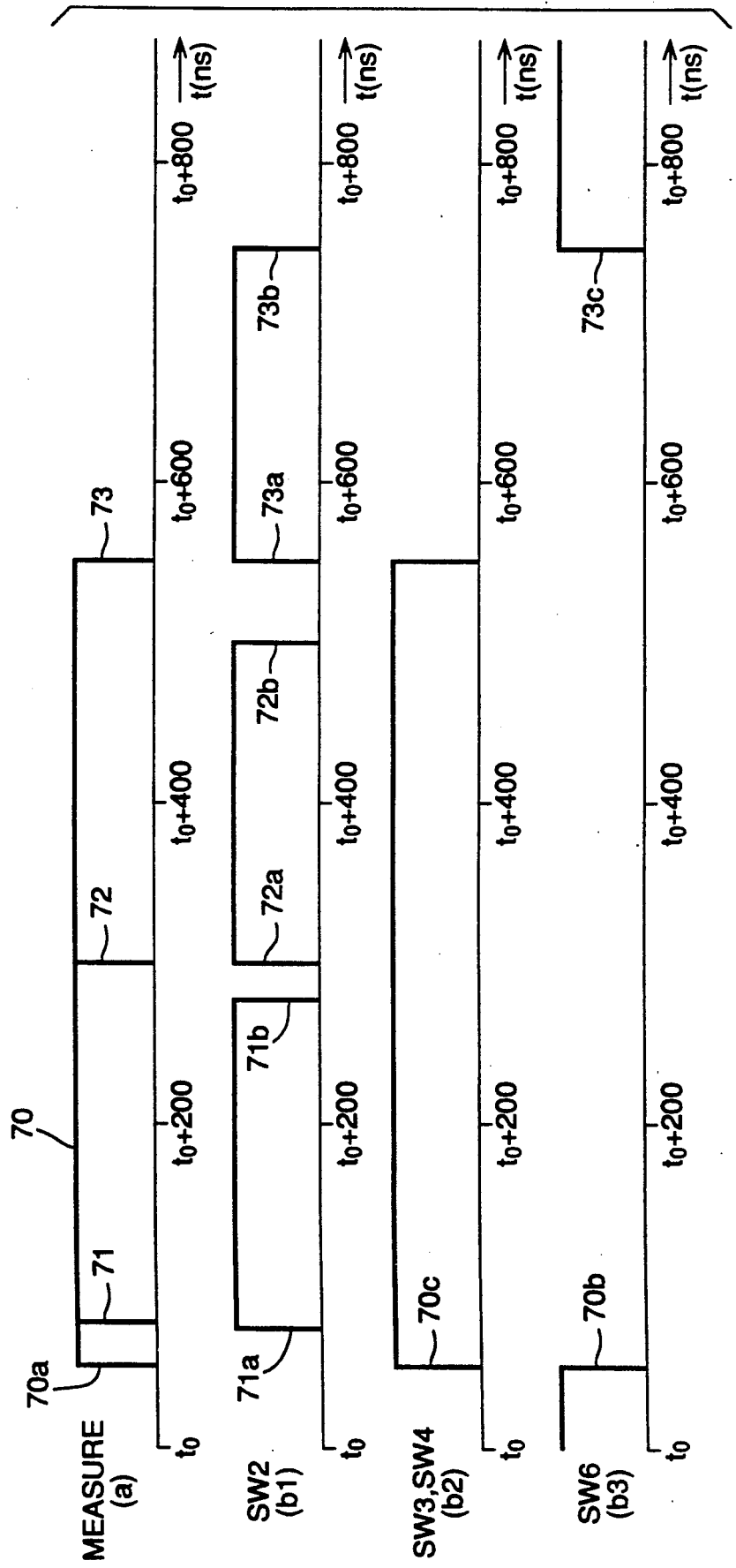
FIG. 5 illustrates waveform timing diagrams which are useful in understanding the operation of a second implementation of the impedance measurement circuit, shown in FIG. 3.

Referring now to FIG. 5, waveform timing diagrams are shown which indicate a second method by which controller 28 may regulate the switches SW2–SW4 and SW6 within the impedance measurement circuit 14 to measure the three different physiological parameters discussed with respect to FIG. 4. The method of FIG. 5 requires a much faster delta modulator 25 than the method of FIG. 4. A delta modulator which is capable of performing the FIG. 5 method must digitize a signal in 200 nanoseconds or less. Referring to line (a) of FIG. 5, the controller samples respiration, patient motion and stroke volume by generating a current pulse 70, beginning at leading edge 70a and lasting a duration of 500 nanoseconds. The controller then directs the measurement of patient motion, respiration and stroke volume by sampling the resulting voltage at the times shown in FIG. 5 by lines 71, 72 and 73, respectively. The controller 28 may regulate continuous sampling of each of the three physiological parameters, sequentially, at preselected intervals (possibly 50 millisecond intervals, as was done in FIG. 4). In a manner similar to the description given with respect to FIG. 4, controller 28 has complete control of the sampling procedure.

Lines (b1)–(b3) of FIG. 5 illustrate one example of a procedure by which controller 28 regulates the sampling of the patient motion, respiration and stroke volume parameters. The controller starts the sampling procedure by opening switch SW6 ((line (b3) goes low)), as shown at 70b, and closing switches SW3 and SW4 ((line (b2) goes high)), as shown at 70c, for a duration which is long enough to sample any of the desired parameters (for example, 500 nanoseconds to measure stroke volume 73). The controller times the duration of the shortest sampling measurement duration, for example 25 nanoseconds to sample the patient motion parameter 71. Next, the controller closes switch SW2, as shown at 71a, to allow the delta modulator 25 (of FIG. 3) to convert the signal to a digital number. SW2 is held closed for the time duration required to digitize the sample (for example, 200 nanoseconds) and then opens, as shown at 71b. In this example, the controller 28 holds switch SW2 open for 25 nanoseconds, as shown between 71b and 72a, after which time the measuring current pulse has been applied for 250 nanoseconds, the time duration of the respiration measurement 72. Again, the controller 28 closes switch SW2, as shown at 72a, for 200 nanoseconds to allow the delta modulator 25 (of FIG. 3) to convert the signal to digital form. The controller 28 then opens switch SW2, as shown at 72b, for 50 nanoseconds, after which time the measuring current pulse has been applied for 500 nanoseconds, the time duration of the stroke volume measurement 73. Next, the controller 28 opens switches SW3 and SW4 and closes switch SW2, as shown at 73a, and the delta modulator 25 (of FIG. 3) converts the stroke volume signal to a digital number. Again, the controller 28 holds SW2 closed 200 nanoseconds. The controller 28 then opens switch SW2, as shown at 73b, and closes switch SW6, as shown at 73c, to finish the sampling procedure and charge the capacitor C2 (of FIG. 3).

From the foregoing description, it is apparent that the circuit of FIG. 3 is a component of an embodiment of the present invention in which a single sensor and circuit is capable of measuring multiple physiological parameters. The timing diagrams of FIG. 5 illustrate that the voltage arising from a single measuring current pulse may be sampled at various times to measure distinct and separate physiological parameters.

Figure 6:
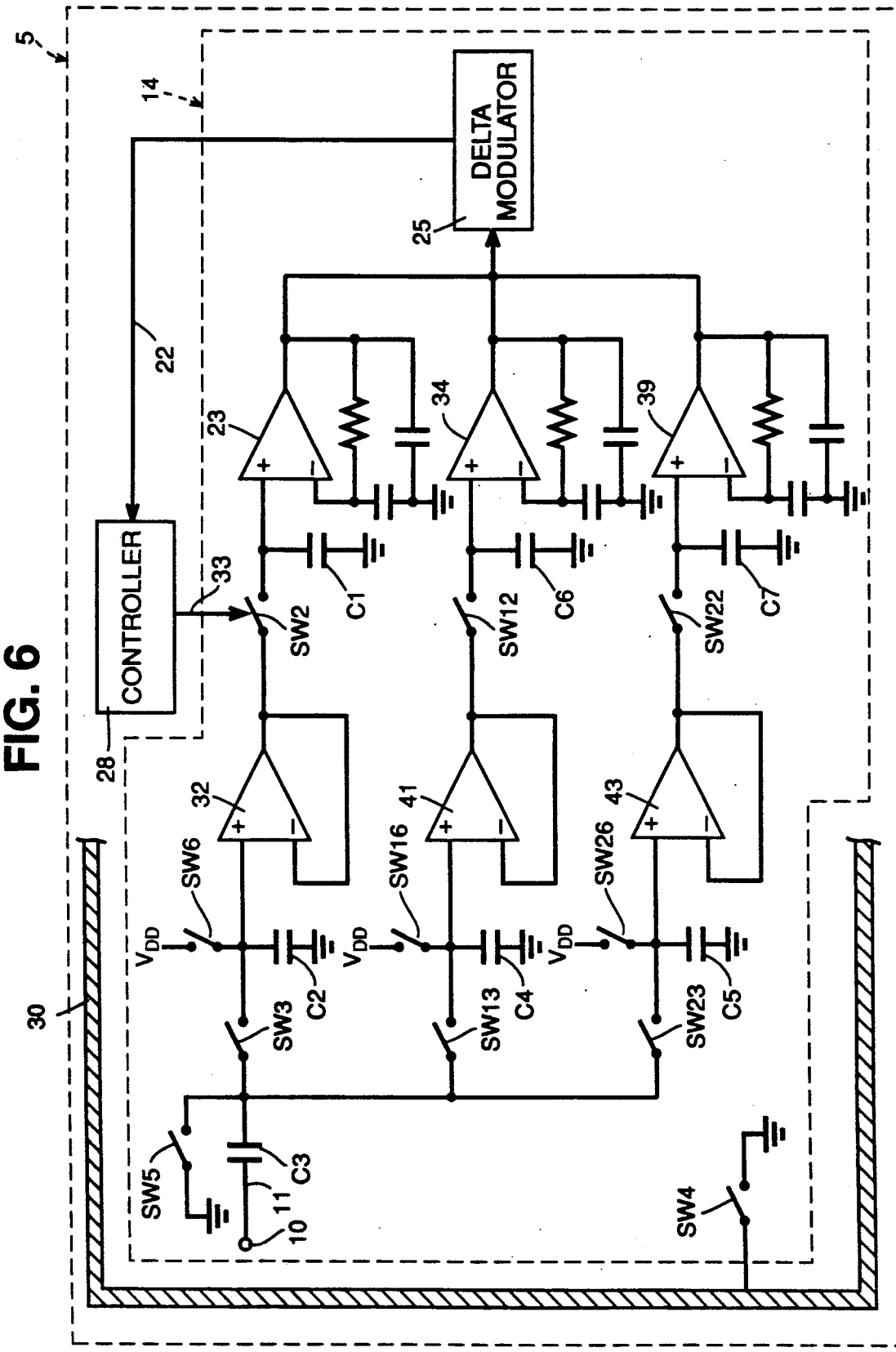
FIG. 6 depicts a second embodiment of an impedance measurement circuit, shown in block form in FIG. 1, which operates in a pulsed mode.

Referring to FIG. 6, an embodiment of the impedance measurement circuit 14, which operates in a manner similar to the circuit of FIG. 3, is shown. The impedance measurement circuit 14 includes a connection through a switch SW4 with the case 30, and connections through switches SW3, SW13 and SW23 with the tip electrode 10 (via the pacing lead 11). As in the case of FIG. 3, the tip electrode 10 is a conventional pacing/sensing electrode and the indifferent electrode is the case 30. Buffers 32, 41 and 43 and filters 23, 34 and 39 (which are discussed hereinafter) are also employed in circuit 14.

All switches in FIG. 6 are controlled by controller 28. One output 33 of the controller is shown extended to switch SW2, but it is to be understood that the switches SW3, SW4, SW5, SW6, SW12, SW13, SW16, SW22, SW23 and SW26 are similarly controlled. The controller closes switches SW6, SW16 and SW26 to charge measuring capacitors C2, C4 and C5 to a regulated voltage source VDD. Subsequently, the controller opens switches SW6, SW16 and SW26 and closes switches SW3 and SW4, while holding switch SW5 open, for a predetermined measuring interval $\Delta T_1$, thereby connecting capacitor C2 to lead 11 through a coupling capacitor C3. While the switches SW3 and SW4 are closed, measuring capacitor C2 discharges through capacitor C3 into the lead 11, thereby decreasing the voltage across measuring capacitor C2. The amount by which the voltage across the measuring capacitor C2 diminishes depends on the impedance of the lead-tip combination and the impedance of the surrounding tissue. The impedance of the lead-tip combination is known and the impedance of the surrounding tissue is the object of the measurement. Measuring capacitor C2 stores the diminished voltage and buffer 32 later transfers this to the measuring circuit in the following manner. After the predetermined measuring time interval $\Delta T_1$, the controller 28 opens switches SW3 and SW4, allowing the buffer 32 to access the voltage held on the measuring capacitor C2. This voltage is advanced through the buffer amplifier 32 and switch SW2 (which the controller 28 closes at the time it opens switches SW3 and SW4), and is sampled on capacitor C1 at the input of the filter 23. The controller 28 holds switch SW2 closed for a time duration which is sufficient for delta modulator 25 to convert the signal into a digital form. After converting the sample to digital form, the controller 28 opens switch SW2 and closes switch SW6 to charge measuring capacitor C2 for the next measurement cycle.

Next, the controller 28 closes switches SW13 and SW4, while holding switch SW5 open, for a second predetermined measuring interval $\Delta T_2$, thereby connecting capacitor C4 to lead 11 through the coupling capacitor C3. While the switches SW13 and SW4 are closed, measuring capacitor C4 discharges through capacitor C3 into the lead 11. Measuring capacitor C4 stores the voltage which buffer 41 later transfers to the measuring circuit. After the predetermined measuring time interval $\Delta T_2$, the controller 28 opens switches SW13 and SW4, allowing the buffer 41 to access the voltage held on the measuring capacitor C12. This voltage is advanced through the buffer amplifier 41 and switch SW12 (which the controller 28 closes at the time it opens switches SW13 and SW4), and is sampled on capacitor C6 at the input of the filter 34. The controller 28 holds switch SW12 closed for a time duration which is sufficient for delta modulator 25 to convert the signal to digital form. After converting the sample to digital form, the controller 28 opens switch SW12 and closes switch SW16 to charge measuring capacitor C4 for the next measurement cycle.

Next, the controller 28 closes switches SW23 and SW4, while holding switch SW5 open, for a third predetermined measuring interval $\Delta T_3$, thereby connecting capacitor C5 to lead 11 through the coupling capacitor C3. While the switches SW23 and SW4 are closed, measuring capacitor C5 discharges through capacitor C3 into the lead 11. Measuring capacitor C5 stores the voltage which buffer 43 later transfers to the measuring circuit. After the predetermined measuring time interval $\Delta T_3$, the controller 28 opens switches SW23 and SW4, allowing the buffer 43 to access the voltage held on the measuring capacitor C22. This voltage is advanced through the buffer amplifier 43 and switch SW22 (which the controller 28 closes at the time it opens switches SW23 and SW4), and is sampled on capacitor C7 at the input of the filter 39. The controller 28 holds switch SW22 closed for a time duration which is sufficient for delta modulator 25 to convert the signal to digital form. After converting the sample to digital form, the controller 28 opens switch SW22 and closes switch SW26 to charge measuring capacitor C5 for the next measurement cycle.

In one embodiment of the invention, the controller 28 measures each physiological parameter twenty times per second. The time duration $\Delta T_1$ is 25 nanoseconds and the voltage measured on capacitor C2 represents a patient motion parameter. The time duration $\Delta T_2$ is 250 nanoseconds and the voltage measured on capacitor C4 represents a respiration parameter. The time duration $\Delta T_3$ is 500 nanoseconds and the voltage measured on capacitor C5 represents stroke volume. The operations of filter 23, capacitor C1 and delta modulator 25 are the same in FIG. 3 and FIG. 6.

The filter 23 preferably filters the impedance signal in such a manner as to favor the sensing of a cardiac hemodynamic signal component over other physiological and non-physiological signal components. To this end, filter 23 filters the impedance signal using a two-pole filter with a center frequency of 1.4 Hz. The gain of filter 23 is reduced by a factor of two (6 dB) at frequencies of 0.2 Hz and 10 Hz.

The filter 34 preferably filters the impedance signal in such a manner as to favor the sensing of a respiration signal component over other physiological and non-physiological signal components. To this end, filter 34 filters the impedance signal using a two-pole filter with a center frequency of 0.2 Hz. The gain of filter 34 is reduced by a factor of two (6 dB) at frequencies of 0.05 Hz and 0.8 Hz. The filter 39 preferably filters the impedance signal in such a manner as to enhance the sensing of a patient motion signal component. To this end, filter 39 filters the impedance signal using a two-pole filter with a center frequency of about 6 Hz. The gain of filter 34 is reduced by a factor of two (6 dB) at frequencies of 5 Hz and 10 Hz.

Figure 7:
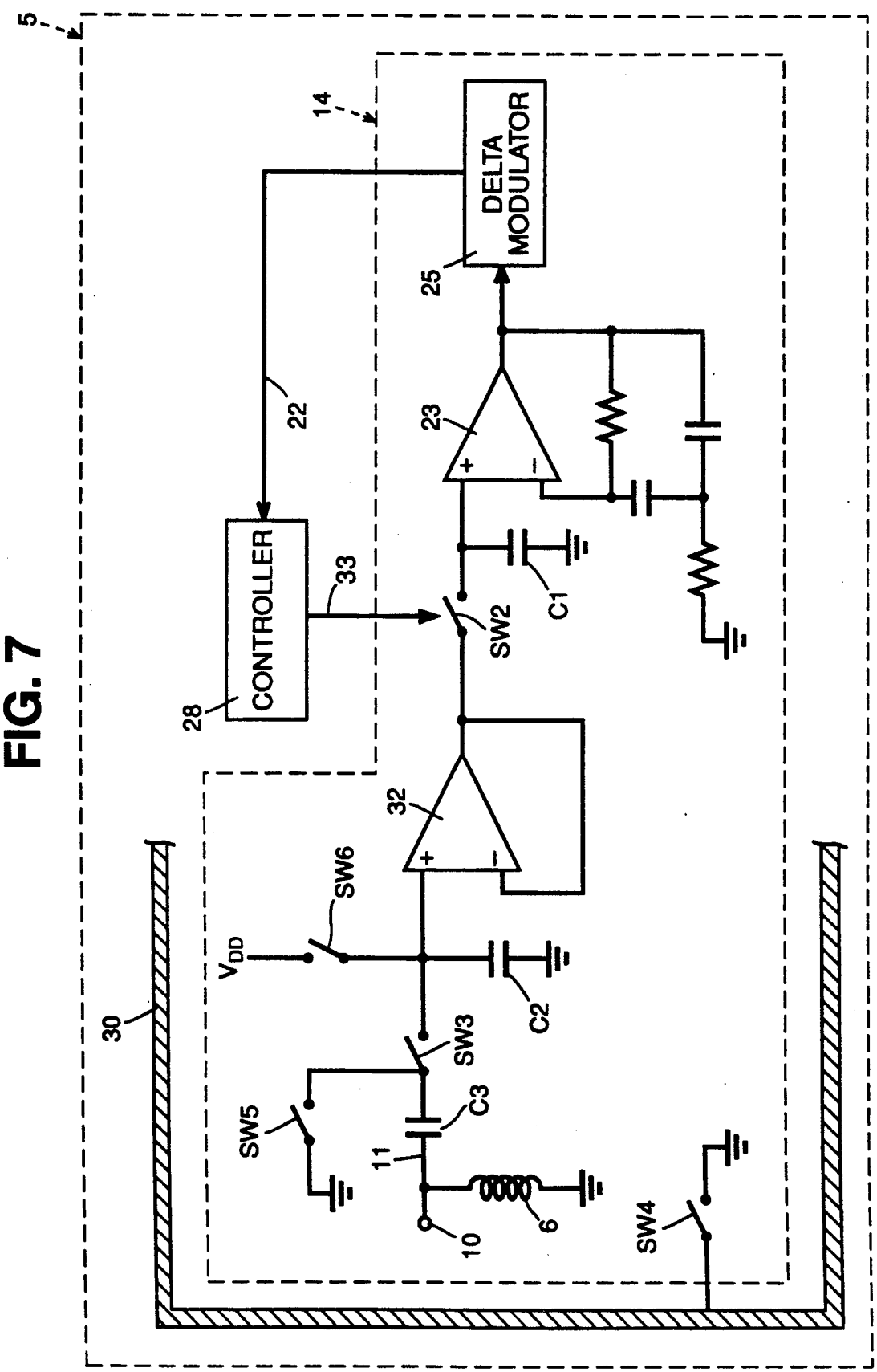
FIG. 7 shows an additional embodiment of an impedance measurement circuit, shown in block form in FIG. 1, which measures impedance by generating a measuring current on a coil, rather than on a lead.

Referring to FIG. 7, another embodiment of the impedance measurement circuit 14, which employs an inductor or coil 6 as an impedance sensor, is shown. The impedance measurement circuits of FIG. 3 and FIG. 7 are identical, except that the circuit of FIG. 7 includes the coil 6 for sensing impedance, while the circuit of FIG. 3 senses impedance by generating current pulses on and measuring the resulting voltage from lead 11. Coil 6 at its proximal end is electrically connected to the lead 11 between the coupling capacitor C3 and the electrode 10. The distal end of the coil 6 may be connected to pacemaker ground. Alternatively, the distal end of the coil 6 may connect to other points within or outside of the circuit. For example, the coil may connect with body fluids of the patient.

The magnitude of the inductance of coil 6, which may range from 10 nH to 1 mH, is selected to provide a high degree of electrical coupling to the tissue. For example, if the inductance is too small, the electrical field energy generated by the coil will be too small to detect changes in impedance which relate to physiological phenomena. Furthermore, the magnitude of the inductance may be varied according to the range of frequencies transmitted into the tissue. For example, an inductance of 10 nH may be employed when a measuring frequency of about 330 MHz is applied to the tissue and an inductance of 1 mH may be used for a measuring frequency of approximately 500 kHz.

The characteristics of the interrogated field may be relevant in determining the physical size of inductor 6. A larger sized inductor may be used to interrogate a specific area, such as a heart valve, a particular blood vessel or a heart chamber. A smaller sized inductor may be used to measure impedance in a more general area or for measuring multiple parameters. Furthermore, the inductor may be selected such that its physical size matches the dimensions of the organ or structure to be interrogated.

The coil 6 can be resonated by appropriate selection of the interrogating frequency and the inductive and capacitive reactance of the circuit to increase the circulating current, thereby enlarging the measured field and raising the sensitivity of the measurement.

The proximal connection of coil 6 may be located at a header (not shown in FIG. 7) of the pacemaker 5. The header is that portion of the pacemaker where the conductor of lead 11 is inserted into a terminal within the body of the pacemaker 5. The coil 6 may be located either externally of the pacemaker case 30 at the header, or internally of the pacemaker case.

Figure 8:
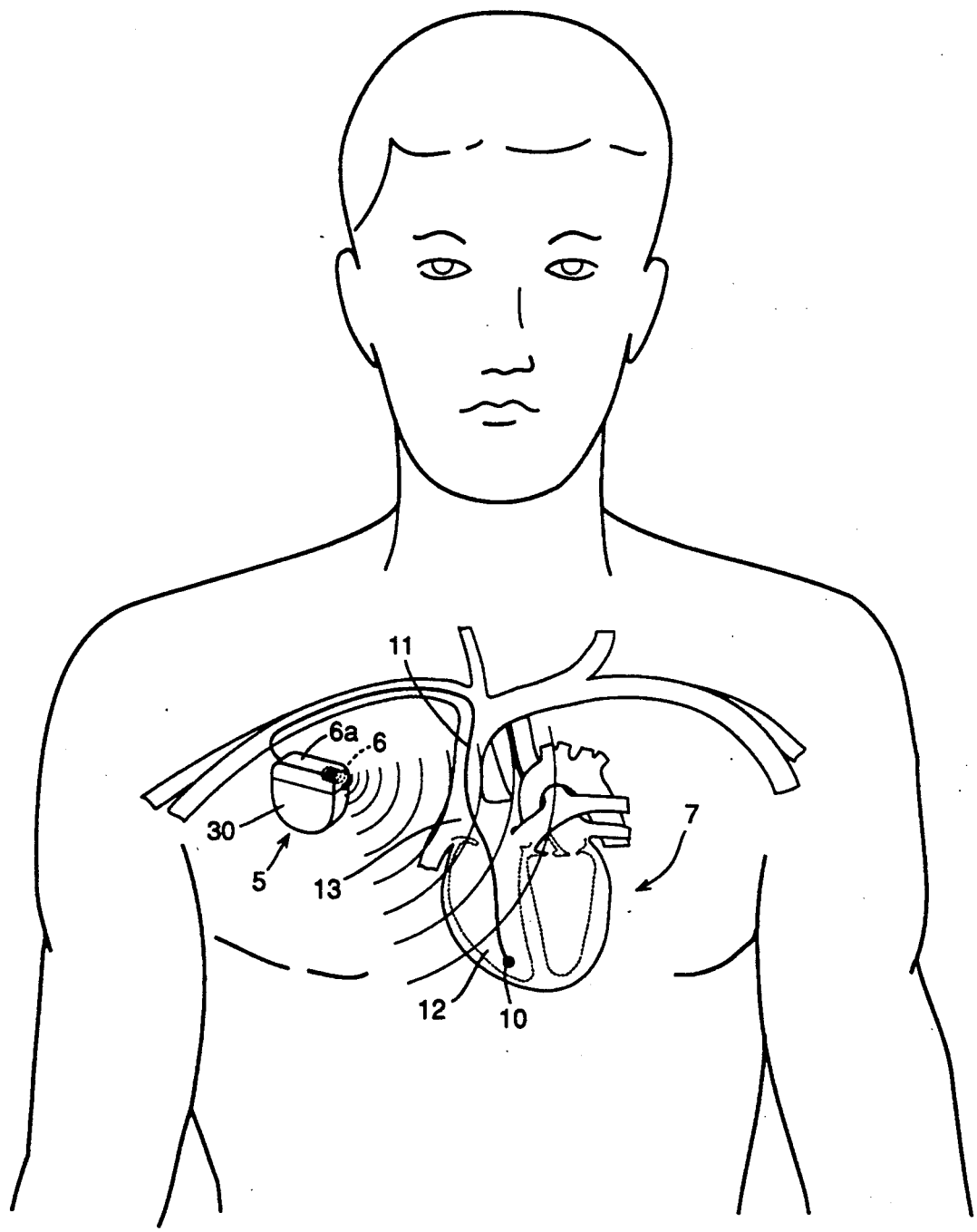
FIG. 8 is an illustration which depicts one method of placement within a patient's body of the coil shown in FIG. 7 for performing an impedance measurement.

FIG. 8 is an illustration which depicts an embodiment of the present invention which employs a coil 6 at the header 6a of the pacemaker 5. The coil 6 is oriented so that it radiates its electrical field toward the patient's pleural area.

Figure 9:
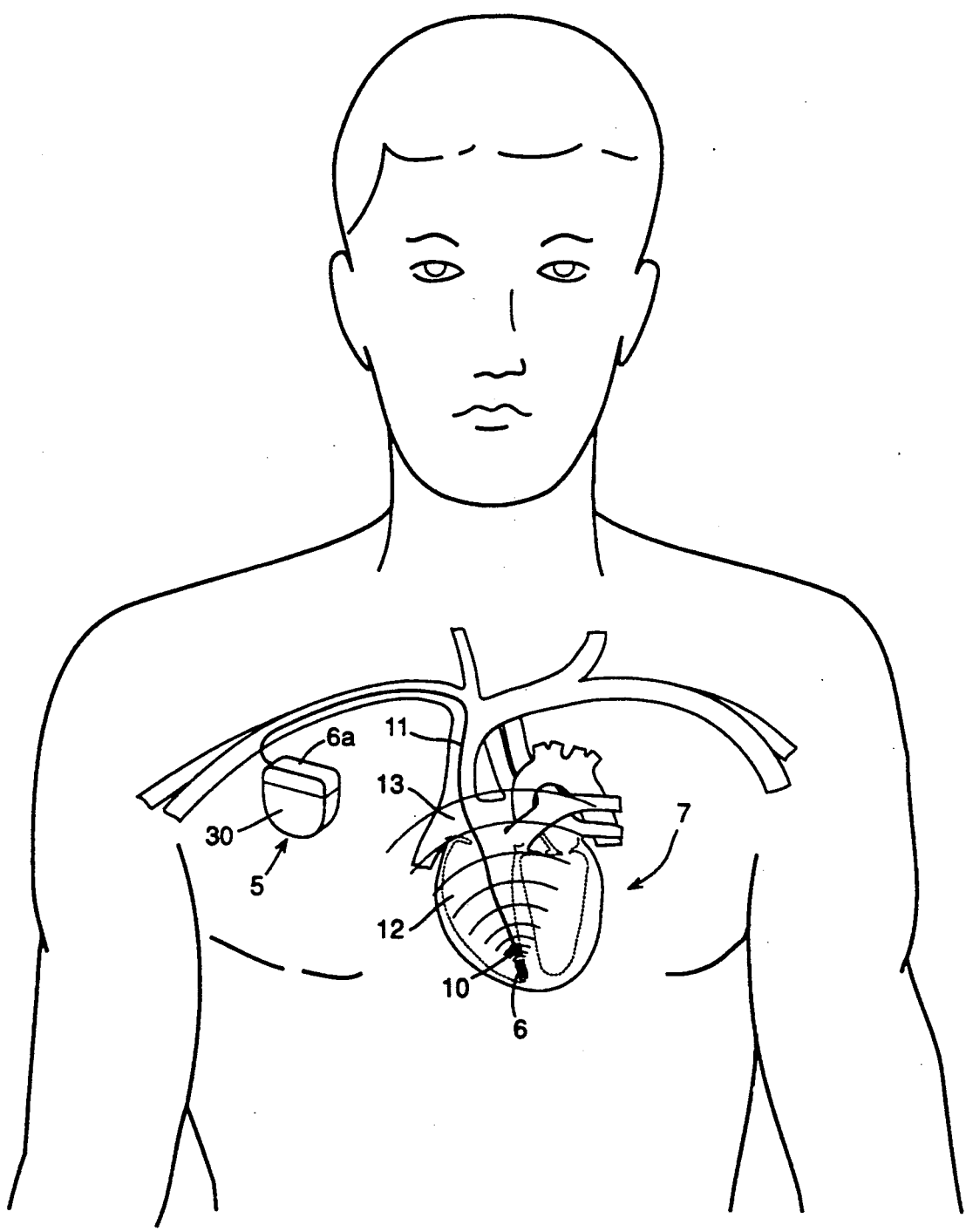
FIG. 9 is an illustration which depicts a second method of placement within a patient's body of the coil shown in FIG. 7 for performing an impedance measurement.

Alternatively, the proximal connection of the coil 6 may be located at the distal end of the lead 11, preferably near the tip electrode 10. FIG. 9 is an illustration which depicts an embodiment of the present invention which employs a coil 6 at the distal end of the lead 11. The coil 6 is directed so that it radiates its electrical field into the patient's heart.

Figure 10:
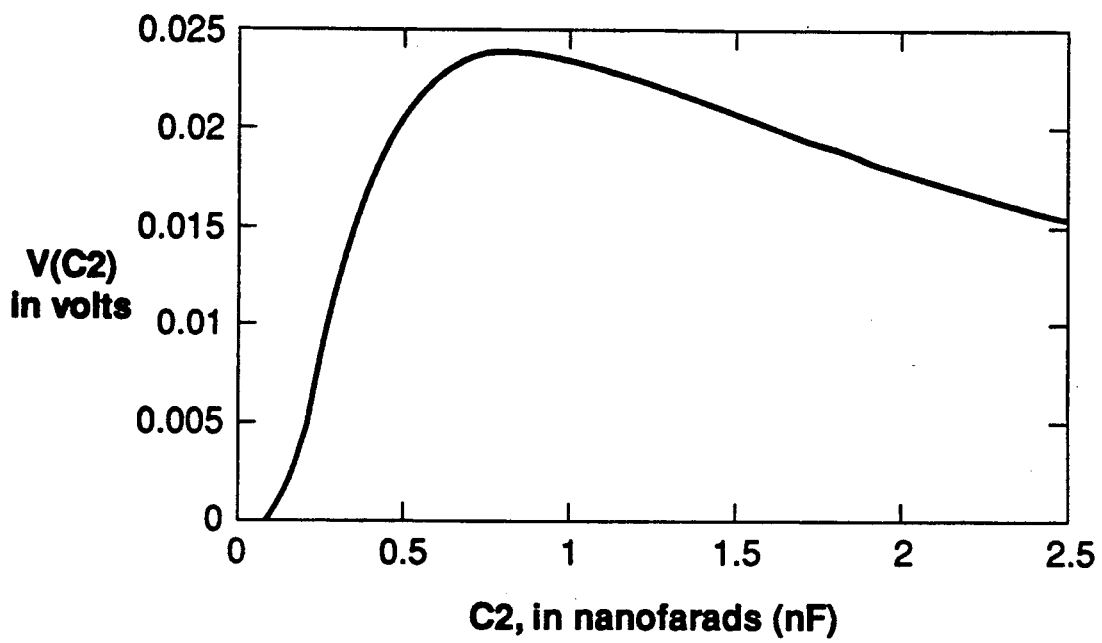
FIG. 10 is a graph illustrating the amplitude of a respiration signal as a function of the sensing capacitance of an impedance measurement circuit, for a given pulse width employing measurements on a pacemaker lead using a circuit which is similar to the circuit of FIG. 3.

FIG. 10 is a graph which illustrates the voltage amplitude V(C2), in volts, of a respiration signal as a function of the source capacitance (the measuring capacitance C2), in nanofarads, of the impedance measuring circuit of FIG. 3. In particular, FIG. 10 shows, for a given capacitor C2 discharge time (a pulse width of 250 ns), the relationship between the change in voltage on the measuring capacitor C2 with respect to the load impedance and the change in load impedance due to respiration. The purpose of FIG. 10 is to show the importance of matching components of the source impedance of an impedance measuring circuit to the load impedance of the body. The capacitive discharge circuit depicted in FIG. 3 operates best with no impedance between the measuring capacitor C2 and the lead 11. Unfortunately, in an implantable pacemaker, a coupling capacitor C3 is generally perceived to be a requirement to assure safety of the patient. Therefore, the value of the measuring capacitor C2 is selected to best match the source impedance, which includes the measuring capacitor C2, with the load impedance, which includes the impedance of the coupling capacitor C3 and the impedance of the lead 11, in combination with the impedance of the body. The impedance measurement from the FIG. 3 capacitive discharge circuit is derived from a direct measurement of voltage across a measuring capacitor C2 as a function of load resistance, the measuring capacitance and the initial voltage across the capacitor. For this capacitive discharge circuit, there exists a preferred measuring capacitance C2 for a given measuring pulse width (for example, 250 ns) and load impedance which will produce a maximum signal voltage V(C2). If the capacitance of the measuring capacitor C2 is very small in comparison to the load impedance of the body, the amplitude of the respiration signal is very small, leading to a modest signal to noise ratio and difficulty in appropriately controlling pacing rate. In contrast, FIG. 10 shows that values of capacitance of the measuring capacitor C2 which are large with respect to load impedance do not greatly diminish the respiratory impedance signal. Therefore, the capacitance of measuring capacitor C2 of an impedance measuring circuit should be equal to or larger than the capacitance which produces a maximum expected respiration signal.

Figure 11:
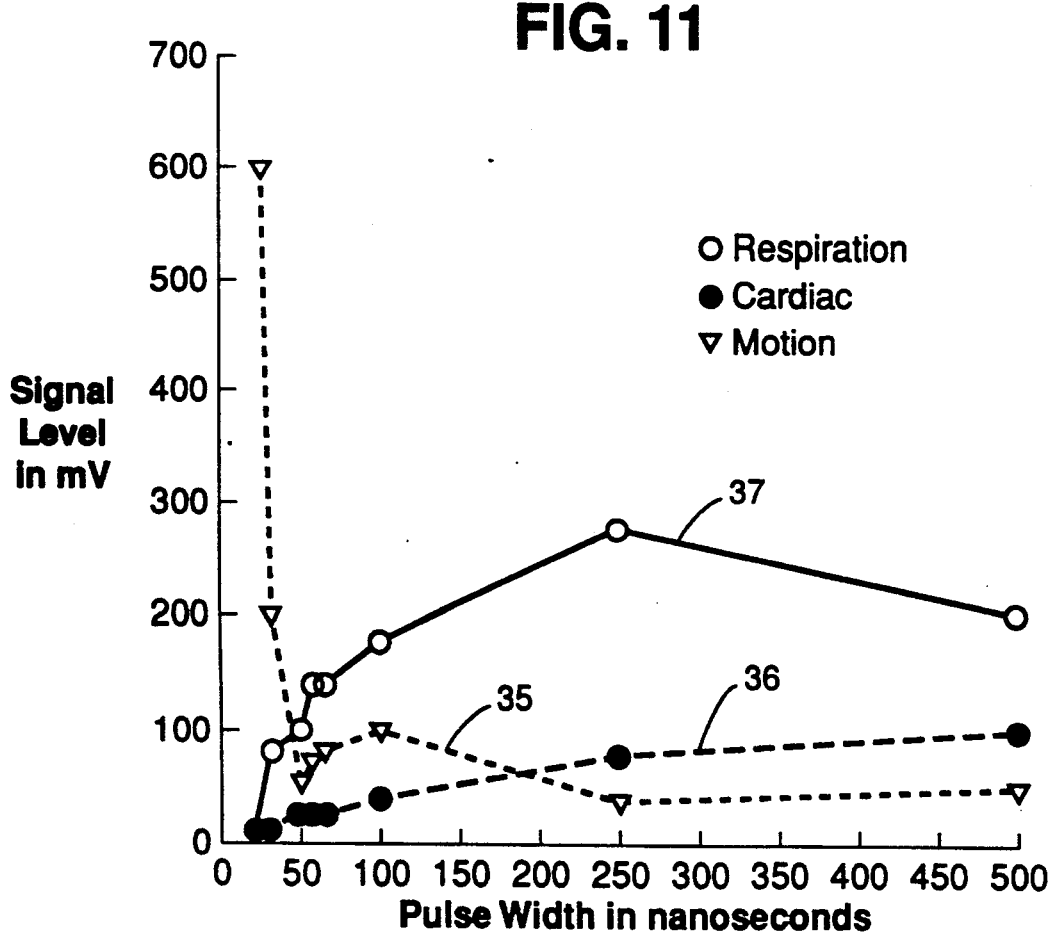
FIG. 11 is a graph which characterizes the relative levels of different physiological and nonphysiological signals which are detected by the circuit of FIG. 3 when it interrogates a patient's body by applying current pulses of various pulse widths to a pacing lead.

The graph of FIG. 11 characterizes the relative levels of different physiological and non-physiological signals which are detected by the circuit of FIG. 3 when it interrogates a patient's body with current pulses of different widths. It illustrates an important advantage of the pacemaker 5 of the present invention. The pacemaker can "tune" the impedance sensor to measure a particular type of signal and reject unwanted signals and other noise by selecting a particular measuring current pulse width. At very short pulse widths (e.g., 60 to 200 nanoseconds) motion artifact signals have the largest amplitude, as shown by "motion" curve 35. The amplitude of physiological signals arising from the heart steadily rises with increasing pulse width duration, as shown by "cardiac" curve 36. The amplitude of respiratory signals abruptly rises with increasing pulse duration to pulse widths of about 250 ns, then decreases for larger pulse width durations, as shown by "respiratory" curve 37. The minute ventilation-controlled metabolic demand pacemaker of the present invention seeks a preferred pulse width of about 250 ns, which provides the best respiratory signal to noise ratio, as is illustrated at 38 in FIG. 12, which figure comprises a graph that illustrates the level of a desired respiratory signal of FIG. 11 relative to a combination of non-respiration "noise" signals of that figure. A pulse width of this duration (250 ns) lessens the influence of cardiac signal "noise", avoids interface electrolytic phenomena, but still reduces the influence of motion artifacts.

Figure 12:
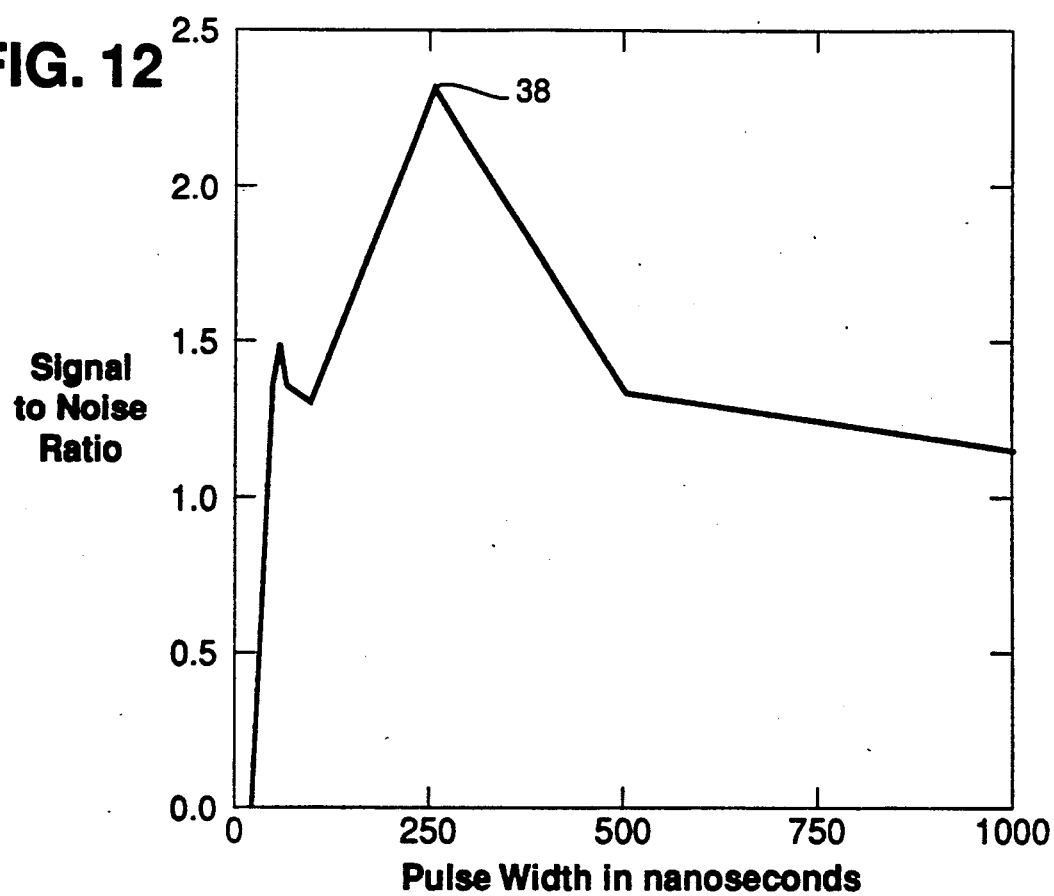
FIG. 12 is a graph which illustrates the level of a respiration signal, shown in FIG. 11, relative to a combination of non-respiration "noise" signals, shown in FIG. 11, as such signals are detected by the circuit of FIG. 3 when it interrogates a patient's body by applying current pulses of various pulse widths to a pacing lead.
Figure 13:
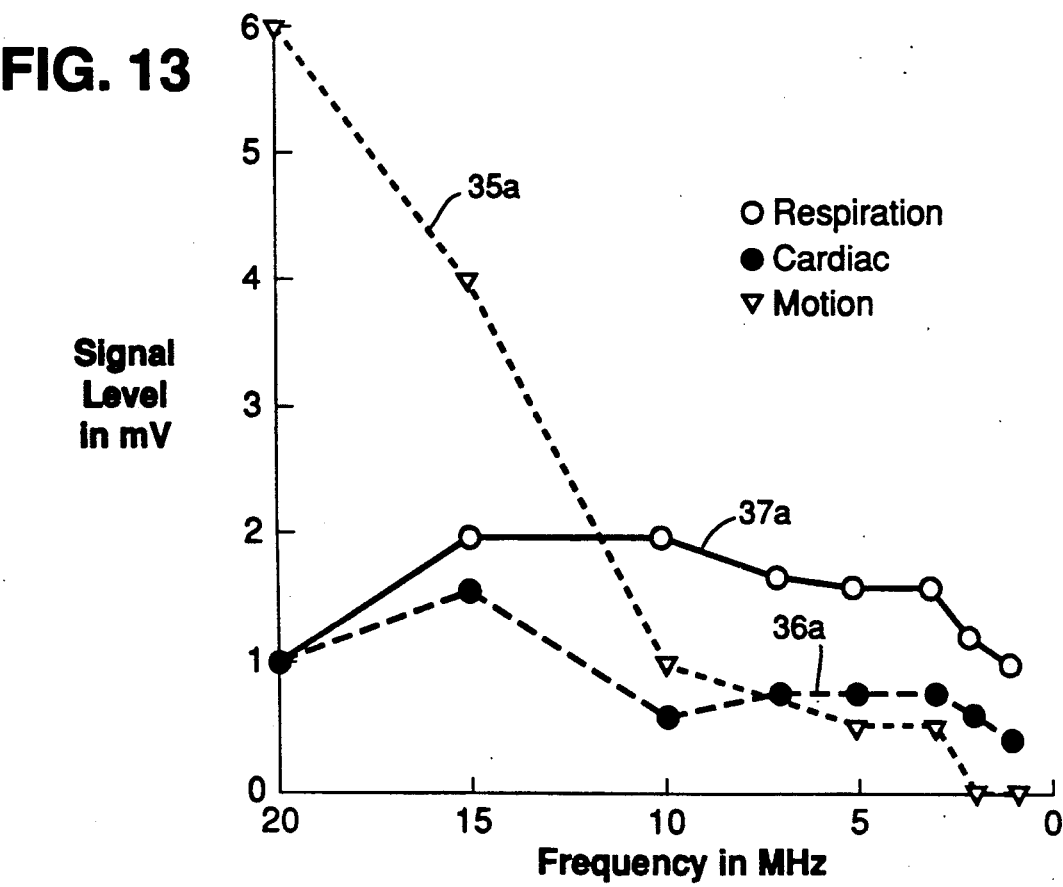
FIG. 13 is a graph which characterizes the relative levels of different physiological and nonphysiological signals a detected by an impedance measurement circuit which interrogates a patient's body with various frequencies of sinusoidal-like oscillating current or timed pulses of sinusoidal-like oscillating current.

FIGS. 11 and 12 exemplify how different pulse widths provide for differentiation of signals arising from various physiological and non-physiological origins. Similarly, FIG. 13 illustrates this phenomenon in a sensing system which employs sinusoidal-like oscillating current modulation rather than discrete current pulses. Shorter pulse widths in a pulsed system have a similar effect upon signal sensing as higher frequencies in a sinusoidal-like oscillating current system. In general, the pacemaker 5 provides the best respiration signal sensing, in comparison with cardiac and motion noise, when the measuring current frequency is about 2 MHz. At higher frequencies, motion artifacts are large and at lower frequencies, cardiac signals obscure the respiration signal.

The graph of FIG. 13 illustrates the signal amplitude arising from various physiological and non-physiological sources as a function of measuring sinusoidal-like oscillating current frequency. "Motion" curve 35a represents the amplitude of motion artifact signals; "cardiac" curve 36a represents the amplitude of physiological signals arising from the heart; and "respiration" curve 37a represents the amplitude of respiratory signals. The pacemaker may deliver these oscillating measuring currents in the form of sinusoidal-like oscillating waves or in the form of timed pulses of oscillating waves. Timed pulses of oscillating waves are discontinuous bursts of oscillating waves which last for a predetermined duration. For example, respiration may be measured by applying a 10 MHz oscillating wave burst lasting a duration of 100 ms. The measurements resulting from both methods are practically the same. To provide timed pulses of sinusoidal-like oscillating measuring current, the pacemaker deactivates the oscillating current to conserve energy, allow sensing of intracardiac electrograms or provide for generation of pacing pulses. The duration of timed pulses of sinusoidal-like oscillating current may range from one cycle of the oscillating frequency to essentially an infinite duration.

The impedance measurement block 14 of FIG. 1 derives digital impedance samples, in the form of 8-bit data bytes having values ranging from −128 to +127, at a rate of 20 per second and communicates these samples to the controller 28 by means of conductor 22. Negative digital signals carried by the conductor 22 indicate that the analog respiration signal is decreasing, while positive digital signals signify an increasing signal. Referring now to FIG. 14, wherein the circuit blocks of controller 28 are shown in greater detail, the manner in which minute volume is derived from the digital samples provided by impedance block 14 will now be considered. An absolute magnitude extractor 40 derives the absolute magnitude of each digital sample (i.e., negatively signed samples are changed to positive samples of the same amplitude). The average value of the digital samples is zero because the filter 23 (FIG. 3) in the impedance measurement block 14 has a gain of zero for a DC input. By eliminating the sign from all samples, an averager 42 derives a running average of the absolute magnitudes of the samples. The time constant of the averager is short (e.g. about 25 seconds) so that the digital value at its output represents the average respiratory tidal volume over a few breaths. The absolute magnitude value of each sample represents the respiratory impedance signal. Therefore, the controller 28 adds and averages a sequence of these absolute magnitude sample values to provide a measure of the respiratory tidal volume.

A sign extractor 44 monitors only the signs, and not the magnitudes, of the digital samples on conductor 22 to provide for zero crossing detection. The sign extractor 44 delivers successive bits, each of which represents the sign of a digital sample, to a zero crossing detector 46. The zero crossing detector 46 monitors respiration rate by ascertaining the timing of changes in the polarity of impedance measurement signal. Generally, a zero crossing occurs whenever the sign of a digital sample differs from the sign of the immediately preceding digital sample. However, there are physiological limits to respiration rate and, therefore, to the frequency of zero crossings. Zero crossings occurring at a rate higher than a predetermined physiological limit must indicate the presence of a noisy respiration signal. Thus, the zero crossing detector analyzes the signs of a number (for example, 10) of the most recently acquired samples and determines whether a defined preponderance of samples (for example, 7 of 10) have a particular sign. If so, and if the last zero crossing operation which found a preponderance of a particular sign determined that the majority had an opposite sign, the zero crossing detector 46 presumes the occurrence of a zero crossing. When the sign changes, the zero crossing detector 46 triggers a sampler 48 to read the average value represented by the current value presented by the averager 42. The sampler 42 delivers this average value to both a short-term averager 50 and a long-term averager 52. In the preferred embodiment of the invention, the short-term averager 50 has a time constant of slightly less than a minute and the long-term averager 52 has a time constant of about one hour.

The zero crossing detector 46 pulses its output twice, and the sampler 48 samples twice, during each breath, when the impedance signal crosses zero during exhalation and during inhalation. The zero crossing detector 46 employs the previously described "majority vote" technique to sense a zero crossing, in which the detector assumes an occurrence of a zero crossing when a predetermined proportion of the most recent samples have a sign opposite to that of the sign determined after the last zero crossing. In the preferred embodiment of the invention, at least 70% of the most recent samples in the last 0.5 second must have a sign opposite to that of the sign determined after the last zero crossing.

Each average value sample at the output of averager 42 represents the tidal volume, the average of the last few integrals of the respiratory impedance signal. The short-term averager 50 and the long-term averager 52 derive values which are dependent not only on the magnitudes of the samples, but also upon the rate of the oscillating respiratory signal, as determined by the zero crossing detector 46. Because the long-term and short-term averagers update and accumulate samples at each zero crossing event, the long-term and short-term minute volume values reflect the rate of breathing as well as the depth of breathing.

As shown in FIG. 14, a summer 54 derives $\Delta MV$, the difference between the short-term averaged and long-term averaged minute volume signals. $\Delta MV$ is the control signal which drives the pacing rate. As the short-term average increases relative to the long-term average, representing an increasing metabolic demand, the pacing rate increases. Conversely, when $\Delta MV$ decreases, the pacing rate decreases.

The $\Delta MV$ value at any instant is the input to a limiter 56, which compares $\Delta MV$ to $\Delta MVMAX$, a predetermined value which serves as the maximum $\Delta MV$ value allowed to control the pacing rate. The limiter 56 applies the current value of $\Delta MV$, or $\Delta MVMAX$ if it is smaller than $\Delta MV$, to the minus input of a summer 58. The summer 58 compares the output of limiter 56 to "maximum interval", a quantity applied at the plus input of summer 58 which represents an offset corresponding to a physician-determined minimum pacing rate. Summer 58 continuously presents its output, a difference value called "respiration" pacing rate 96, to the input of a rate control block 95, which compares and analyzes derived pacing rates, for example "cardiac" rate 98 and "activity" rate 97 as determined by other physiological signal processors which are to be described hereinafter, to determine a pacing rate for stimulating the patient's heart. The rate control block 95 uses this pacing rate, in combination with a SENSE signal 24 from the sense amplifier 16 of FIG. 1 to determine when to deliver a pace signal 26 to the pulse generator 18 of FIG. 1.

In this manner, the pacemaker operates in a standard VVI mode except that the minute volume measurement may determine the pacing rate. As the quantity $\Delta MV$ increases, the summer 58 derives a smaller difference value ("maximum interval" minus $\Delta MV$) that it presents to rate control block 95. This, in turn, means that the pacing rate increases, as is required for a larger $\Delta MV$. When $\Delta MV$ is zero, the summer 58 presents the "maximum interval" value to the rate control block 95, which results in the minimum pacing rate, precisely what is required when there is no metabolic demand beyond that provided by the minimum pacing rate. The quantity "maximum interval" is simply the interval which corresponds to the minimum rate.

Timing for the rate control block 95 is provided by a clock 64 which applies pulses to a divider 66. The divider 66 divides the clock pulses by a quantity referred to as a prescaler and produces a count signal on line 62 which extends to the rate control block 95.

Conventional pacemakers include telemetry systems, as represented by block 68 of FIG. 14, which allow a physician to program parameters such as minimum rate, as well as the prescaler value, $\Delta MVMAX$ and the reference threshold which is applied to a comparator 60, as will be described below. The method of derivation of these programmable parameters is disclosed in the description of the '725 pacemaker.

Again referring to FIG. 14, the output of summer 54 is input, not only to the limiter 56, but also to the plus input of comparator 60. The telemetrically-programmed reference threshold feeds the minus input of the comparator. Whenever $\Delta MV$ exceeds the reference threshold, the output of the comparator goes high and inhibits the long-term averager 52. In effect, a large value of $\Delta MV$ represents a metabolic demand which is associated with an exercising patient. Until the patient stops exercising, the long-term average does not increase. If it were allowed to increase, after an hour or more the long-term average would approach the value of the short-term average, $\Delta MV$ would diminish and the pacing rate would drop from its original high value. Once the patient begins exercising and the pacing rate increases, it is not desirable that the rate decrease simply due to the elapse of time. For this reason, the pacemaker fixes the long-term average. When the patient stops exercising and the short-term average decreases, $\Delta MV$ will fall below the reference threshold and the long-term average will again track the short-term average in the usual manner. In the illustrative embodiment of the invention, the reference threshold is equal to one-half of the ΔMVMAX, unless the physician programs the value differently. This technique allows long-term adaptation to a basal minute volume measurement level while still allowing extended periods of exercise.

Figure 15:
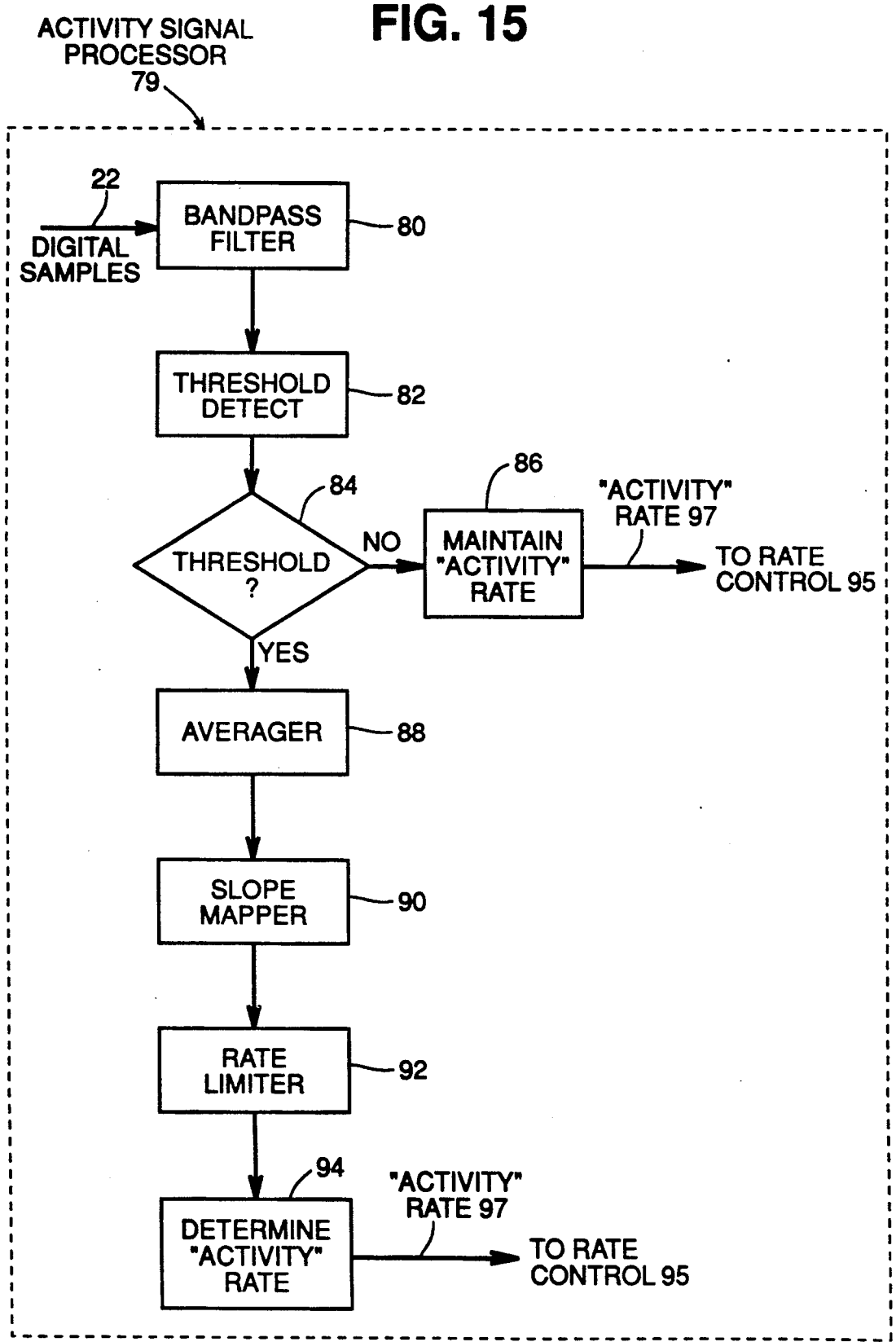
FIG. 15 depicts a flow chart of operations performed by a controller, shown in block form in FIG. 1, which operate on digital samples of the impedance measurement to derive "activity" rate commands that are sent to a rate controller.

Referring now to FIG. 15, wherein the functional blocks, designated generally as an activity signal processor 79, performed by controller 28 are shown in greater detail. The flow chart of FIG. 15 illustrates the manner in which the controller 28 derives the value of patient motion, or activity, from the digital samples 22 provided by impedance block 14 of FIGS. 3, 6 or 7. The activity signal processor 79 reads digital samples 22 and applies them to a bandpass filter 80 which rejects low and high frequency components of the digital signal. Next, a threshold detect block 82 compares the filtered signal amplitude to a preset threshold value. Under the control of threshold logic block 84 and a maintain "activity" rate block 86, if the signal does not surpass the threshold value, an "activity" pacing rate 97 is set to a predetermined baseline rate and sent to the rate controller 95, which comprises another group of function blocks that are performed by the controller 28. If the filtered signal is larger than the threshold value, averager block 88 sums or digitally integrates the digital sample value over a selected time period to determine a time average of the activity signal. Next the averaged signal extends to a slope mapper 90 which converts the current processed activity sample value to a pacing rate value, according to a predetermined and selected linear or nonlinear slope relationship. A rate limiter block 92 compares this pacing rate value to preselected upper and lower limits and, if the rate is outside the limits, will set the pacing rate to the appropriate limit.

Next, a determine "activity" rate block 94 sets the pacing rate which is determined according to the activity measurement. Block 94 may set the "activity" rate 97 to the rate from the rate limiter 92 or may provide rate smoothing or averaging of the "activity" rate if the difference between the current and most recent rates differ by more than a predetermined amount.

Telemetric programming by a physician may be used to program the selected time period, slope, upper and lower pacing rates and rate smoothing variables.

Figure 16:
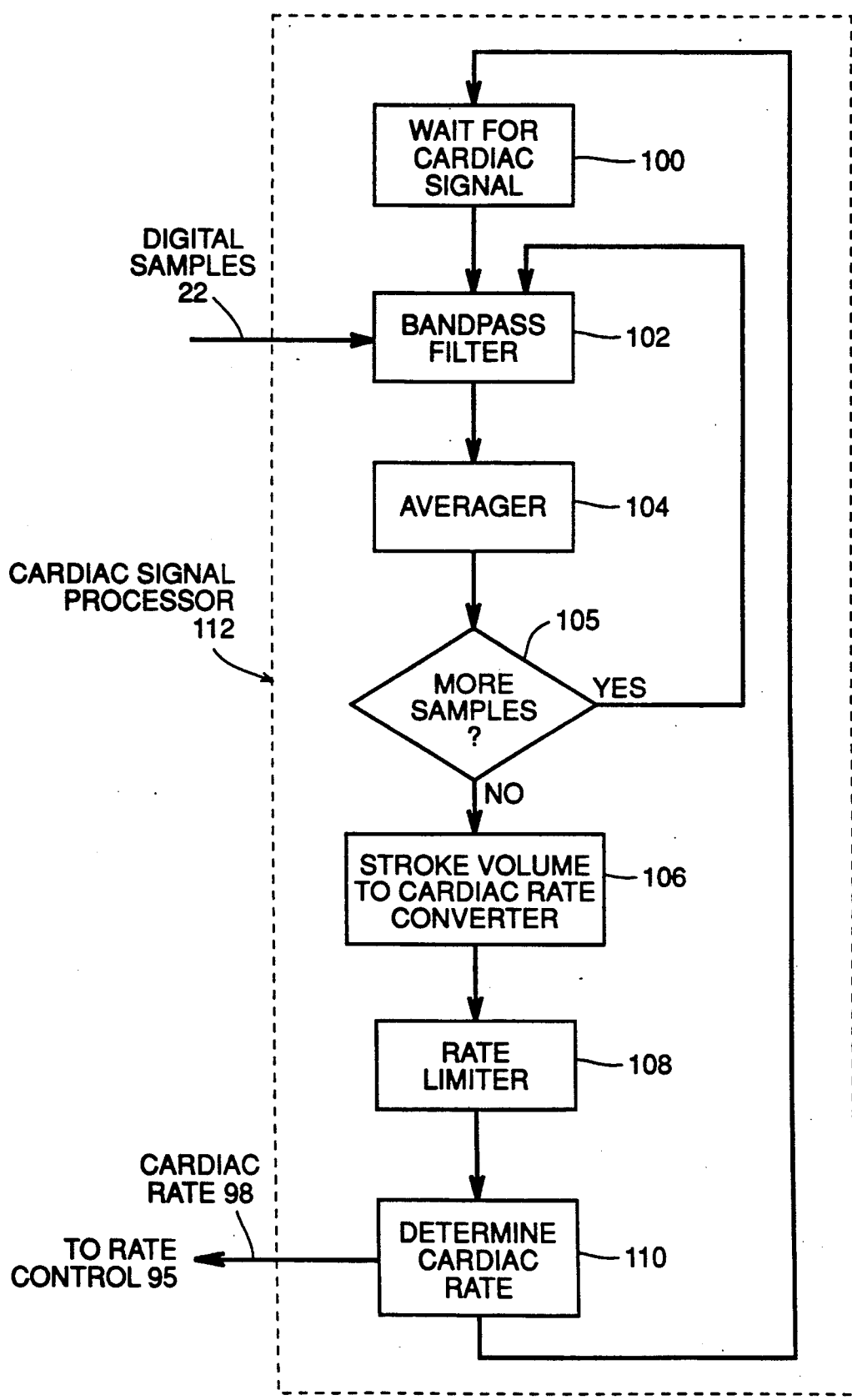
FIG. 16 depicts a flow chart of operations, performed by a controller shown in block form in FIG. 1, which operate on digital samples of the impedance measurement to derive "cardiac" rate commands that are sent to a rate controller.
Figure 17A:
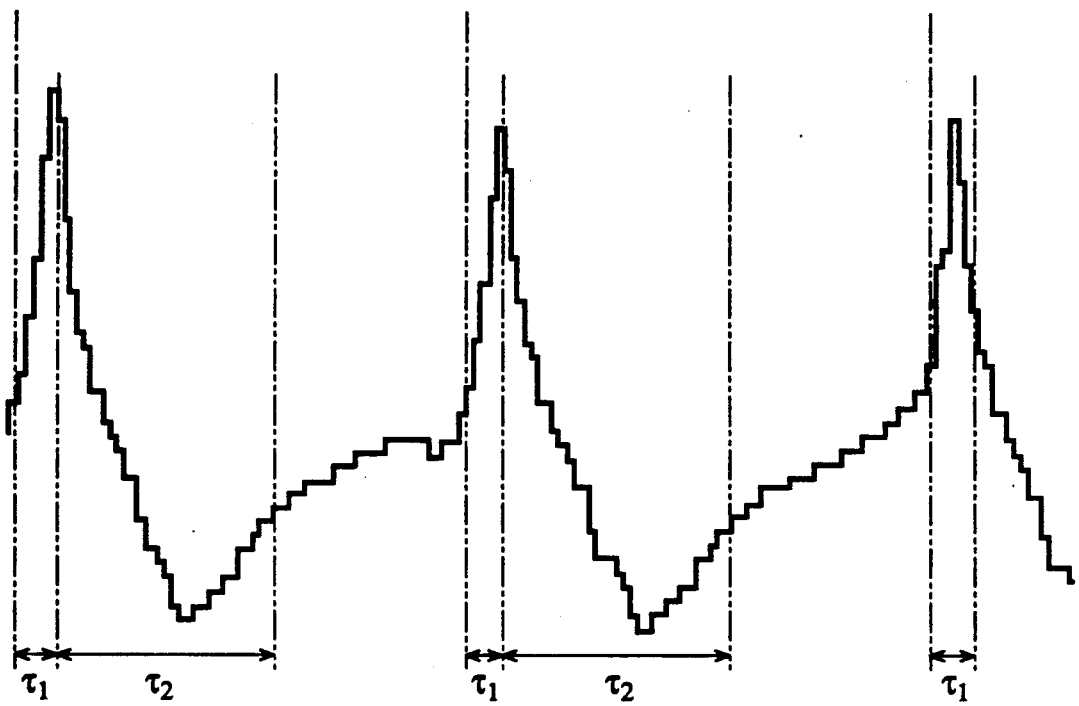
FIGS. 17A and 17B are, respectively, an illustration of a sample intracardiac electrogram signal indicating normal sinus rhythm cardiac behavior and an illustration of a cardiac hemodynamic signal, which show the timing relationship between the two signals.
Figure 17B:
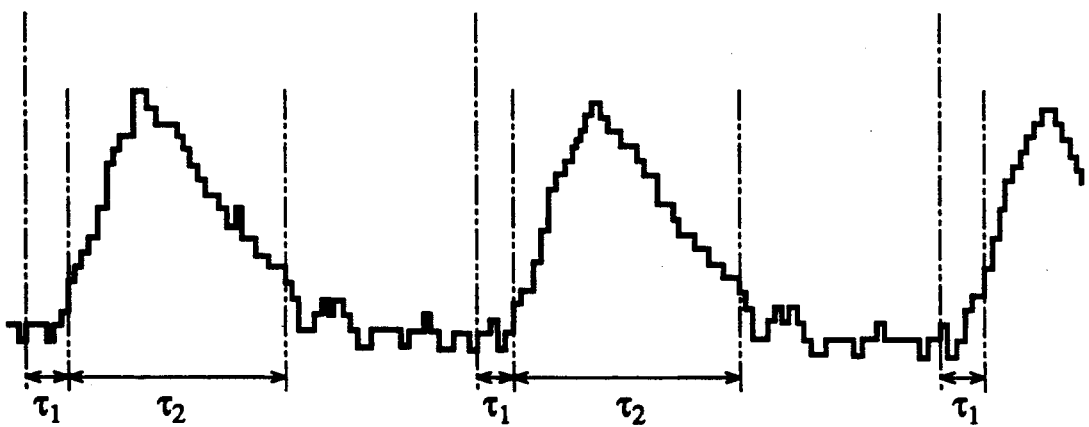

Referring now to FIG. 16, wherein the functional blocks, designated generally as a cardiac signal processor 112, performed by controller 28 are shown in greater detail. The flow chart illustrates the manner in which the controller 28 analyzes the digital samples 22 provided by the impedance block 14 of FIGS. 3, 6 or 7 and derives the value of cardiac rate signal 98 which is indicative of the patient's stroke volume. Referring to FIG. 1 in conjunction with FIG. 16, in wait for cardiac signal block 100, the controller 28 waits for the occurrence of either a PACE signal on line 26 or a SENSE signal on line 24, and then, in either case, waits a predetermined delay time $\tau_1$ before performing bandpass filter block 102. FIG. 17A is an illustration of an intracardiac electrogram signal portraying an intrinsic cardiac signal which evokes a SENSE signal on line 24. FIG. 17B is an illustration of a cardiac hemodynamic signal which results from the heart depolarization characterized in the intracardiac electrogram of FIG. 17A. During wait for cardiac signal block 100, the controller waits for the delay period $\tau_1$ to expire, as is shown in FIG. 17B. The controller 28 samples the cardiac signal only for the time $\tau_2$ when a hemodynamic signal is present following a cardiac electrical event (PACE or SENSE). The controller 28 sets the predetermined delay time $\tau_1$ to correspond to the time between the cardiac electrical event and the mechanical ejection of blood from the heart. The delay following a SENSE signal may be different from the delay after a PACE signal.

Following the triggering signal and delay period, the cardiac signal processor 112 (FIG. 16) reads digital samples 22 and applies them to a bandpass filter 102 which rejects low and high frequency components of the digital signal. Averager block 104 sums or digitally integrates the digital sample value over a selected time period $\tau_2$, which is illustrated in FIG. 17B, to determine a time average of the stroke volume signal. During the time interval $\tau_2$, the controller 28 controls the sampling rate of the digital samples. A preferred sampling rate is approximately 100 Hz, although the controller 28 regulates sampling rates in the range from 20 Hz to 200 Hz. The preferred sampling time interval $\tau_2$ is 200 milliseconds, although the controller 28 confines this interval to range from 25 milliseconds to 250 milliseconds.

Averager block 104 counts the number of samples processed in bandpass filter block 102 and averager block 104 to correlate the same with the stroke volume signal time period $\tau_2$. If more samples are to be processed in this cardiac cycle, more samples logic block 105 returns control of the procedure to bandpass filter block 102 to process another sample. Otherwise, the cardiac signal processor 112 performs the stroke volume to cardiac rate converter 106 operation. The averager block 104 provides any required time and amplitude scaling to appropriately correlate the cardiac and respiration signals. The stroke volume to cardiac rate converter 106 converts the current processed stroke volume sample value to a rate.

In the preferred embodiment of the invention, the stroke volume to heart rate converter 106 determines heart rate from the stroke volume measurement by one of three methods. A physician may select a desired one of such methods by telemetric programming. According to a first method, the stroke volume to heart rate converter 106 derives the pacing rate by determining a value for the average stroke volume at rest, $S_{Ravg}$, through time averaging of stroke volume values which have been accumulated only when the cardiac rate, either sensed or stimulated, is below a predetermined resting rate, $HR_{rest}$. The stroke volume to heart rate converter 106 continuously derives a short-term average stroke volume, $S_{ST}$, by averaging stroke volume values, regardless of heart rate, only over a short time (for example, 20 seconds). The stroke volume to heart rate converter 106 then subtracts the average stroke volume at rest ($S_{Ravg}$) from the short-term average stroke volume, $S_{ST}$, to determine the increment in stroke volume, $S_{inc}$. The stroke volume to heart rate converter 106 sets $S_{inc}$ to zero if it is otherwise negative. In general, an increasing metabolic demand causes an elevation in stroke volume, but an increasing heart rate from pacing causes a decrease in stroke volume. Therefore, the stroke volume to heart rate converter 106 increases pacing rate as the increment in stroke volume, $S_{inc}$, increases until an increment in pacing rate causes a reduction in $S_{inc}$. When this occurs, the stoke volume to heart rate converter 106 lessens the pacing rate by a predefined rate decrement and holds the pacing rate at this level for a predetermined length of time before further raising the pacing rate.

According to a second method, the stroke volume to heart rate converter 106 derives the pacing rate by determining a value for the average cardiac output at rest, $CO_{Ravg}$. According to this method, the stroke volume to heart rate converter 106 multiplies stroke volume values by heart rate to determine an instantaneous cardiac output value, CO. CO samples are accumulated to provide $CO_{Ravg}$ only when the cardiac rate, either sensed or stimulated, is below the predetermined resting rate, $HR_{rest}$. The stroke volume to heart rate converter 106 continuously derives a short-term average cardiac output, $CO_{ST}$, by averaging CO values, regardless of heart rate, only over a short time (for example, 20 seconds). The stroke volume to heart rate converter 106 then subtracts the average cardiac output at rest ($CO_{Ravg}$) from the short-term average cardiac output, $CO_{ST}$, to determine the increment in cardiac output, $CO_{inc}$. The stroke volume to heart rate converter 106 sets $CO_{inc}$ to zero if it is otherwise negative. Cardiac output must increase with pacing rate, otherwise the pacing rate should no longer increase. Therefore, the stroke volume to heart rate converter 106 increases pacing rate as the increment in cardiac output, $CO_{inc}$, increases until an increment in pacing rate causes a reduction in $CO_{inc}$. When this occurs, the stoke volume to heart rate converter 106 reduces the pacing rate by a predefined rate decrement and holds the pacing rate at this level for a predetermined length of time before further raising the pacing rate.

According to a third method, the stroke volume to heart rate converter 106 does not independently change the pacing rate, but rather allows the pacing rate to be determined by the other rate processors, either the activity signal processor or the respiration signal processor. In this method, the stroke volume to heart rate converter 106 continuously determines the increment in cardiac output, $CO_{inc}$, in the manner of the second method described above. If the pacing rate, as determined by the non-cardiac signal processor, increments the pacing rate while $CO_{inc}$ is decreasing, the stroke volume to heart rate converter 106 will decrease the pacing rate by a predefined rate decrement and holds the pacing rate at this level for a predetermined length of time before further raising the pacing rate.

Assuming that the stroke volume to heart rate converter 106 sets a pacing rate in accordance with one of the methods described above, a rate limiter block 108 compares this pacing rate value to preselected upper and lower limits and, if the rate is outside the limits, will set the "cardiac" pacing rate to the appropriate limit.

Next, a determine "cardiac" rate block 110 sets the pacing rate which is determined according to the stroke volume measurement. Block 110 may set the "cardiac" rate to the rate from the rate limiter 108 or may provide rate smoothing or averaging of the "cardiac" rate if the difference between the current and most recent rates differ by more than a predetermined amount.

As in the case of the respiration and activity signal processors, telemetric programming by a physician may be used to program the selected time period, slope, upper and lower pacing rates and rate smoothing variables.

Figure 18:
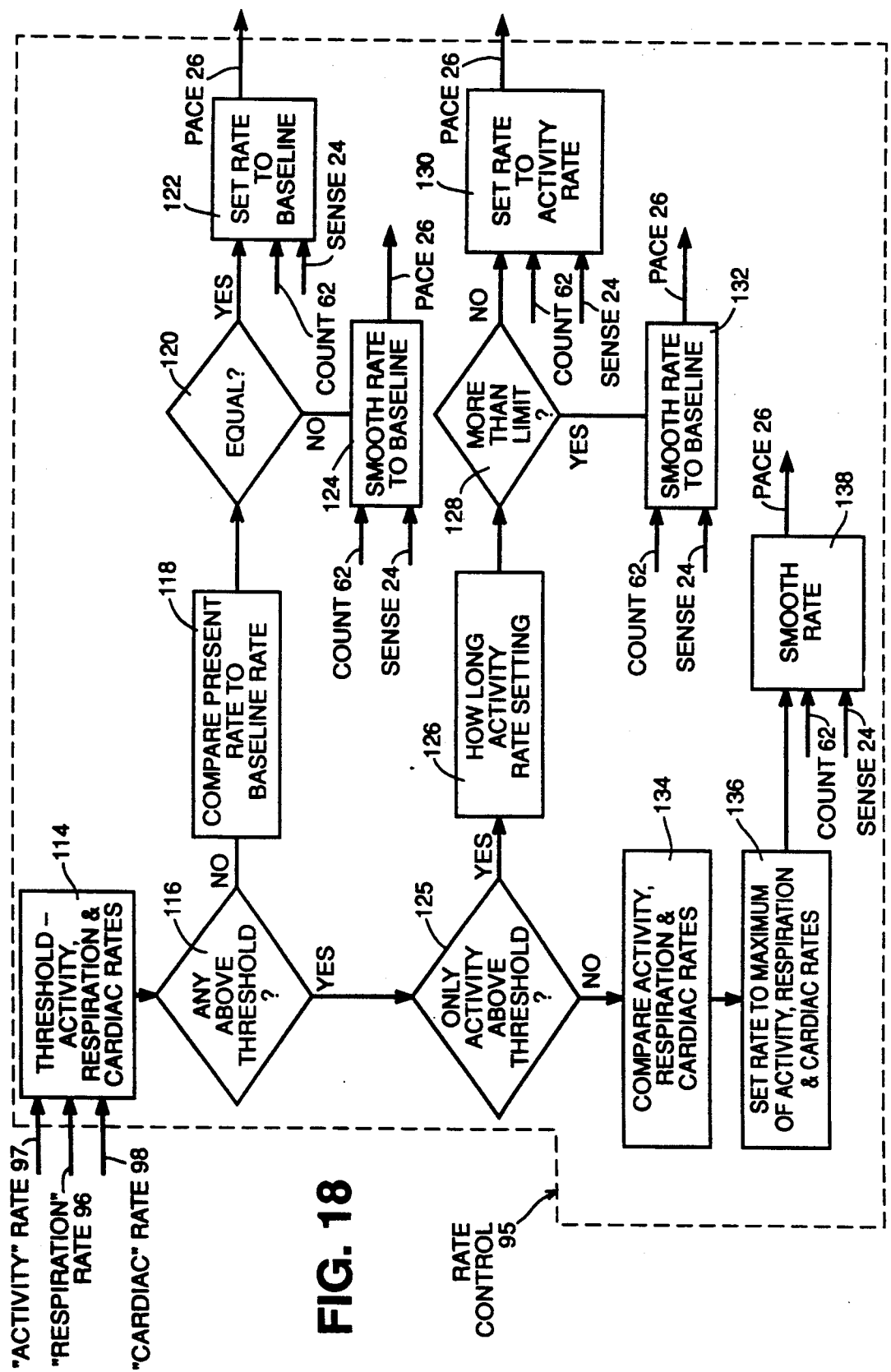
FIG. 18 depicts a flow chart of operations performed by a controller, shown in block form in FIG. 1, with respect to the "respiration" rate, "activity" rate, and "cardiac" rate commands determined in the operations of FIG. 14, FIG. 15 and FIG. 16, respectively, to derive pace commands that are sent to a pulse generator, also shown in block form in FIG. 1.

Referring to FIG. 18, wherein the functional blocks performed by rate control block 95 of FIG. 14 are shown in greater detail, rate control block 95 analyzes the pacing rates from the various physiological signal processors to determine an operational pacing rate. A threshold block 114 reads the "activity" rate 97, "respiration" rate 96 and "cardiac" rate 98 inputs and compares each rate with a corresponding activity, respiration and cardiac rate threshold. Under the control of logic block 116, if none of the rates are above the corresponding threshold value, a compare present rate to baseline rate block 118 compares the present rate to a predetermined and preprogrammed baseline pacing rate. Under the control of logic block 120, if the present rate is equal to the baseline rate, a set rate to baseline block 122 sets the pacing rate for the next cardiac cycle to the baseline rate. Block 122 (as well as blocks 124, 130, 132 and 138, which are described below) includes access to a timer (not shown) which the controller 28 loads with the most recently determined operational pacing rate. This operation takes place upon the occurrence of either of two events, a SENSE signal upon conductor 24 or the countdown to zero of timer 62.

In this manner the count 62 pulses, which act upon the decrement input of the timer, occur at a rate slower than the clock rate. The count in the timer decrements whenever a pulse appears at the output of divider 66 in FIG. 14. When the timer decrements to zero, it produces a pulse upon PACE conductor 26 to trigger activity of the pulse generator 18 in FIG. 1. If the sense amplifier 16 of FIG. 1 senses a natural heartbeat before the timer decrements to zero, the timer will not produce a pulse on PACE conductor 26. In either case, the timer loads the pacing rate which is set within rate control block 95 to initialize the escape interval of the pacemaker. The escape interval is the time between a paced or sensed cardiac event and the subsequent pacing stimulus. If the present rate is not equal to the baseline rate, smooth rate to baseline block 124 may determine the difference between the present rate and the baseline rate and perform rate smoothing to gradually decrement the pacing rate to the baseline level. Programming of the rate control block 95 may also designate that no rate smoothing is to occur, in which case, block 124 will set the pacing rate to the baseline level. Block 124 acts in the manner of block 122 to operate the timer and generate pace 26 signals which activate the pulse generator 18.

Referring back to logic block 116, if one or more of the physiological pacing rates did exceed its corresponding threshold rate, logic block 125 determines whether the activity rate was the only parameter above its threshold rate. The rate control block 95 performs an extra check on the activity parameter because it is inherently susceptible to activation by noisy or nonphysiological signals. If activity is the only parameter providing a rate which is above threshold, how long activity rate setting block 126 determines how long activity has been the only operative signal. Under the control of logic block 128, if this condition has persisted for longer than a predetermined duration, smooth rate to baseline block 132 smoothes (averages) the pacing rate to the baseline rate in the manner of block 124. If the activity rate has not been the only operative signal for the prescribed duration, set rate to activity rate block 130 employs the "activity" rate to set the operational pacing rate and generate pace 26 signals for the page generator 18 in the manner of block 122. It is desirable to allow the activity physiological parameter to drive the pacing rate because its sensor reacts to stimulation very rapidly. However, that the activity signal persists while no other sensor responds is an indication of no true physiological stimulation.

Also under the control of logic block 125, if any sensor other than the activity sensor produces a rate above its threshold rate, block 134 compares the derived "activity", "respiration" and "cardiac" rates. Block 136 sets the pacing rate to the fastest of these rates. Block 138 then issues a pace 26 signal to the pace generator 18 and may be programmed to gradually smooth the pacing rate from its current level to its derived level.

From the foregoing discussion, it is apparent that the present invention provides rate-responsive pacing based on measurements of respiratory minute volume, patient motion or activity, and cardiac mechanical signals corresponding to stroke volume which are sensed from a standard pacing lead using a single sensor. The invention accomplishes substantial improvements in the determination of a physiological pacing rate by employing the sensing of multiple physiological parameters using a single impedance transducer.

Although the invention has been described with reference to particular embodiments, it is to be understood that such embodiments are merely illustrative of the application of the principles of the invention. Numerous modifications may be made therein and other arrangements may be devised without departing from the true spirit and scope of the invention.

What is claimed is:

1. A metabolic demand rate-responsive cardiac stimulation apparatus, comprising:
    means for pacing a patient's heart at a controlled rate;
    means for measuring impedance within the patient's body, said impedance measuring means including means for applying multiple fixed frequencies of measuring currents between two points within said apparatus and means for measuring voltages in response to the application of said measuring currents, said measuring currents having frequency components within a range of from approximately 10 kilohertz to approximately 1000 megahertz;
    means for controlling said impedance measuring means to limit the frequency components of the applied measuring currents to lie within at least one predetermined subrange of frequencies such that the measured voltage within each subrange of frequencies corresponds to a measurement of a metabolic demand parameter;
    means for deriving at least one metabolic demand parameter from the measured voltage corresponding to each of said at least one predetermined subrange of frequencies; and
    means for determining said controlled pacing rate in relation to the values of said at least one derived metabolic demand parameter.

2. An apparatus according to claim 1, wherein said pacing means includes at least one pacing lead, wherein said impedance measuring means includes a means for generating a measuring current, and wherein said current generating means and said voltage measuring means are coupled to said at least one pacing lead.

3. An apparatus according to claim 1, wherein said apparatus further comprises an inductance coil, wherein said impedance measuring means includes a means for generating a measuring current, and wherein said current generating means and said voltage measuring means are coupled to said coil.

4. An apparatus according to claim 1, wherein said measuring current applying means includes a circuit which generates a constant measuring current.

5. An apparatus according to claim 1, wherein said measuring current applying means includes a circuit which generates a measuring current using a constant voltage.

6. An apparatus according to claim 1, wherein said impedance measuring means includes means for generating measuring currents in the form of short-duration, square-wave-like current pulses.

7. An apparatus according to claim 6, wherein said impedance measuring means includes means for generating measuring current pulses having pulse durations in the range from 5 nanoseconds to 20 microseconds.

8. An apparatus according to claim 6, wherein said controlling means includes means for limiting said impedance measuring means to generate measuring current pulses having pulse durations within at least one predetermined subrange of durations.

9. An apparatus according to claim 8, further including second and third derived metabolic demand parameters, wherein said at least one derived metabolic demand parameter is based on patient motion and its associated subrange of pulse durations includes durations shorter than approximately 125 nanoseconds; wherein said second metabolic demand parameter is based on respiration and its associated subrange of pulse durations includes durations from approximately 50 nanoseconds to approximately 400 nanoseconds; and wherein said third metabolic demand parameter is based on cardiac hemodynamic signals and its associated subrange of pulse durations includes durations longer than approximately 300 nanoseconds.

10. An apparatus according to claim 9, wherein said means for deriving a metabolic demand parameter includes means for deriving a metabolic demand parameter based on respiration, and wherein said metabolic demand parameter is selected from a group including respiratory rate, respiratory tidal volume and respiratory minute ventilation.

11. An apparatus according to claim 9, wherein said means for deriving a metabolic demand parameter includes means for deriving a metabolic demand parameter based on cardiac hemodynamic signals, and wherein said metabolic demand parameter is selected from a group including paced depolarization gradient, stroke volume and cardiac output.

12. An apparatus according to claim 1, wherein said impedance measuring means includes means for generating measuring currents in the form of short-duration, square-wave-like current pulses, wherein said controlling means includes means for regulating said impedance measuring means to generate measuring current pulses having a predetermined pulse duration, said regulating means regulating, for each of said measuring current pulses, at least one subrange of sampling times with respect to the onset of the current pulse at which said impedance measuring means measures the voltage evoked by the current pulse, and wherein said at least one subrange of sampling times defines a sampling frequency which corresponds to a measurement of a metabolic demand parameter.

13. An apparatus according to claim 12, further including second and third derived metabolic demand parameters, wherein said at least one derived metabolic demand parameter is based on patient motion and its associated subrange of sampling times includes times shorter than approximately 125 nanoseconds; wherein said second metabolic demand parameter is based on respiration and its associated subrange of sampling times includes times from approximately 50 nanoseconds to approximately 400 nanoseconds; and wherein said third metabolic demand parameter is based on cardiac hemodynamic signals and its associated subrange of sampling times includes times longer than approximately 300 nanoseconds.

14. An apparatus according to claim 13, wherein said means for deriving a metabolic demand parameter includes means for deriving a metabolic demand parameter based on respiration, and wherein said metabolic demand parameter is selected from a group including respiratory rate, respiratory tidal volume and respiratory minute ventilation.

15. An apparatus according to claim 13, wherein said means for deriving a metabolic demand parameter includes means for deriving a metabolic demand parameter based on cardiac hemodynamic signals, and wherein said metabolic demand parameter is selected from a group including paced depolarization gradient, stroke volume and cardiac output.

16. An apparatus according to claim 1, wherein said impedance measuring means includes means for generating measuring currents in the form of sinusoidal-like oscillating currents.

17. An apparatus according to claim 16, wherein said impedance measuring means includes means for generating measuring oscillating currents having frequency components in the range from 10 kilohertz to 1000 megahertz.

18. An apparatus according to claim 16, wherein said controlling means includes means for limiting said impedance measuring means to generate measuring currents having sinusoidal-like oscillating frequencies within at least one predetermined subrange of frequencies.

19. An apparatus according to claim 18, further including second and third derived metabolic demand parameters, wherein said at least one derived metabolic demand parameter is based on patient motion and its associated subrange of sinusoidal-like oscillating frequencies includes frequencies higher than approximately 8 megahertz; wherein said second metabolic demand parameter is based on respiration and its associated subrange of oscillating current frequencies includes frequencies from approximately 1 megahertz to approximately 11 megahertz; and wherein said third metabolic demand parameter is based on cardiac hemodynamic signals and its associated subrange of oscillating current frequencies includes frequencies lower than approximately 4 megahertz.

20. An apparatus according to claim 19, wherein said means for deriving a metabolic demand parameter includes means for deriving a metabolic demand parameter based on respiration, and wherein said metabolic demand parameter is selected from a group including respiratory rate, respiratory tidal volume and respiratory minute ventilation.

21. An apparatus according to claim 19, wherein said means for deriving a metabolic demand parameter includes means for deriving a metabolic demand parameter based on cardiac hemodynamic signals, and wherein said metabolic demand parameter is selected from a group including paced depolarization gradient, stroke volume and cardiac output.

22. An apparatus according to claim 1, wherein said impedance measuring means includes means for generating measuring currents in the form of timed pulses of sinusoidal-like oscillating current.

23. An apparatus according to claim 22, wherein said impedance measuring means includes means for generating timed pulses of an oscillating measuring current having timed pulses of durations of at least 5 nanoseconds and having frequency components in the range of from 10 kilohertz to 1000 megahertz.

24. An apparatus according to claim 23, wherein said controlling means includes means for limiting said impedance measuring means to generate measuring currents having oscillating frequencies within at least one predetermined subrange of frequencies.

25. A method for pacing a rate-responsive cardiac stimulation apparatus at a rate determined by a patient's metabolic demand, comprising the steps of:
measuring impedance within the patient's body, said impedance measuring step comprising the substeps of applying multiple fixed frequencies of measuring currents between two points within the apparatus and measuring voltages in response to the application of said measuring currents, said measuring currents having frequency components within a range from approximately 10 kilohertz to approximately 1000 megahertz;
controlling the measuring frequency components of the applied measuring currents to lie within at least one predetermined subrange of frequencies such that the measured voltage within each subrange of frequencies corresponds to a measurement of a metabolic demand parameter;
deriving at least one metabolic demand parameter from the measured voltage corresponding to each of said at least one predetermined subrange of frequencies;
determining a controlled pacing rate in relation to the values of said at least one derived metabolic demand parameter; and
pacing a patient's heart at said controlled rate.

26. A method according to claim 25, wherein said apparatus includes at least one pacing lead and wherein said impedance measuring step includes the substeps of:
applying said measuring current to said at least one lead; and
measuring the resulting voltage appearing at an input to said at least one lead.

27. A method according to claim 25, wherein said apparatus includes an inductance coil and wherein said impedance measuring step includes the substeps of:
applying said measuring current to said coil; and
measuring the resulting voltage appearing at an input to said coil.

28. A method according to claim 25, wherein said impedance measuring step includes the substep of generating said measuring currents in the form of short-duration, square-wave-like current pulses.

29. A method according to claim 25, wherein said impedance measuring step includes the substep of generating said measuring currents in the form of short-duration, square-wave-like current pulses having pulse durations in the range of from 5 nanoseconds to 20 microseconds.

30. A method according to claim 29, wherein said controlling step includes the substep of regulating said impedance measuring step to generate measuring current pulses having pulse durations within at least one predetermined subrange of durations.

31. A method according to claim 29, wherein said deriving step derives second and third metabolic demand parameters, and wherein said controlling step includes the substep of regulating said impedance measuring step to generate measuring current pulses having pulse durations within predetermined subranges of durations, said at least one derived metabolic demand parameter being based on patient motion and having its associated subrange of durations include pulse durations shorter than approximately 125 nanoseconds, said second metabolic demand parameter being based on respiration and having its associated subrange durations include pulse durations from approximately 50 nanoseconds to approximately 400 nanoseconds, and said third metabolic demand parameter being based on cardiac hemodynamic signals and having its associated subrange of durations include pulse durations longer than approximately 300 nanoseconds.

32. A method according to claim 31, wherein said step of deriving a metabolic demand parameter includes the substep of deriving a metabolic demand parameter based on respiration, said metabolic demand parameter being selected from a group including respiratory rate, respiratory tidal volume and respiratory minute ventilation.

33. A method according to claim 31, wherein said step of deriving a metabolic demand parameter includes the substep of deriving a metabolic demand parameter based on cardiac hemodynamic signals, said metabolic demand parameter being selected from a group including paced depolarization gradient, stroke volume and cardiac output.

34. A method according to claim 31, wherein said controlling step includes the substeps of regulating said impedance measuring step to generate measuring current pulses having a predetermined pulse duration and regulating, for each of said measuring current pulses, at least one subrange of sampling times with respect to the onset of the current pulse at which said impedance measuring step measures the voltage evoked by the current pulse, said at least one subrange of sampling times defining a sampling frequency which corresponds to a measurement of a metabolic demand parameter.

35. A method according to claim 25, wherein said impedance measuring step generates measuring currents in the form of sinusoidal-like oscillating currents.

36. A method according to claim 35, wherein said impedance measuring step generates oscillating measuring currents having frequency components in the range of from 10 kilohertz to 1000 megahertz.

37. A method according to claim 36, wherein said controlling step includes the substep of limiting said impedance measuring step to generating measuring currents having oscillating current frequencies.

38. A method according to claim 35, wherein said deriving step derives second and third metabolic demand parameters, and wherein said controlling step includes the substep of limiting said impedance measuring step to generate measuring currents having oscillating current frequencies within at least one predetermined subrange of frequencies, said at least one derived metabolic demand parameter being based on patient motion and having its associated subrange of oscillating current frequencies include frequencies higher than approximately 8 megahertz, said second metabolic demand parameter being based on respiration and having its associated subrange of oscillating current frequencies include frequencies from approximately 1 megahertz to approximately 11 megahertz, and said third metabolic demand parameter being based on cardiac hemodynamic signals and having its associated subrange of oscillating current frequencies include frequencies lower than approximately 4 megahertz.

39. A method according to claim 38, wherein said step of deriving a metabolic demand parameter includes the substep of deriving a metabolic demand parameter based on respiration, said metabolic demand parameter being selected from a group including respiratory rate, respiratory tidal volume and respiratory minute ventilation.

40. A method according to claim 38, wherein said step of deriving a metabolic demand parameter includes the substep of deriving a metabolic demand parameter based on cardiac hemodynamic signals, said metabolic demand parameter being selected from a group including paced depolarization gradient, stroke volume and cardiac output.

41. A method according to claim 25, wherein said impedance measuring step includes the substep of generating measuring currents in the form of timed pulses of sinusoidal-like oscillating currents.

42. A method according to claim 41, wherein said impedance measuring step includes the substep of generating timed pulses of sinusoidal-like oscillating current having timed pulses of durations of at least 5 nanoseconds and having frequency components in the range from 10 kilohertz to 1000 megahertz.

43. A method according to claim 42, wherein said controlling step includes the substep of limiting said impedance measuring step to generate measuring currents having oscillating current frequencies within at least one predetermined subrange of frequencies, and wherein the measured voltage within each subrange of frequencies corresponds to a measurement of a metabolic demand parameter.

44. A method for pacing a rate-responsive cardiac stimulation apparatus at a rate determined by a patient's metabolic demand, comprising the steps of:

measuring impedance within the patient's body, said impedance measuring step comprising the substeps of applying multiple fixed frequencies of measuring voltages between two points within the apparatus and measuring currents in response to the application of said measuring voltages, said measuring voltages having frequency components within a range from approximately 10 kilohertz to approximately 1000 megahertz;

controlling the measuring frequency components of the applied measuring voltages to lie within at least one predetermined subrange of frequencies such that the measured current within each subrange of frequencies corresponds to a measurement of a metabolic demand parameter;

deriving at least one metabolic demand parameter from the measured current corresponding to each of said at least one predetermined subrange of frequencies;

determining a controlled pacing rate in relation to the values of said at least one derived metabolic demand parameter; and pacing a patient's heart at said controlled rate.

* * * * *